(12) United States Patent
Haskell et al.

(10) Patent No.: US 7,886,575 B2
(45) Date of Patent: *Feb. 15, 2011

(54) HIGH SENSITIVITY ACOUSTIC WAVE MICROSENSORS BASED ON STRESS EFFECTS

(75) Inventors: Reichl B Haskell, Nashua, NH (US); Daniel S Stevens, Stratham, NH (US); Jeffrey C Andle, Falmouth, ME (US)

(73) Assignee: Delaware Capital Formation, Inc., Wilmington, DE (US)

( * ) Notice: Subject to any disclaimer, the term of this patent is extended or adjusted under 35 U.S.C. 154(b) by 487 days.

This patent is subject to a terminal disclaimer.

(21) Appl. No.: 11/875,162

(22) Filed: Oct. 19, 2007

(65) Prior Publication Data

US 2008/0163694 A1    Jul. 10, 2008

Related U.S. Application Data

(60) Provisional application No. 60/863,871, filed on Nov. 1, 2006.

(51) Int. Cl.
   *G01N 29/02* (2006.01)
(52) U.S. Cl. .................. 73/24.01; 73/24.06
(58) Field of Classification Search ............ 73/24.06, 73/31.05, 31.06, 599, 24.01
See application file for complete search history.

(56) References Cited

U.S. PATENT DOCUMENTS

| | | | |
|---|---|---|---|
| 4,361,026 A | 11/1982 | Muller et al. | |
| 4,928,513 A | 5/1990 | Sugihara et al. | |
| 5,129,262 A | 7/1992 | White et al. | |
| 5,208,504 A | 5/1993 | Parker et al. | |
| 5,323,636 A | 6/1994 | McGowan et al. | |
| 5,345,201 A | 9/1994 | Greer et al. | |
| 5,365,770 A * | 11/1994 | Meitzler et al. ............ | 73/24.06 |
| 5,445,008 A | 8/1995 | Wachter et al. | |
| 5,719,324 A | 2/1998 | Thundat et al. | |

(Continued)

FOREIGN PATENT DOCUMENTS

GB    2 117 115 A    10/1983

(Continued)

OTHER PUBLICATIONS

PCT Search Report dated Apr. 7, 2009 of Patent Application No. PCT/US2008/080263 filed Oct. 17, 2008.

(Continued)

*Primary Examiner*—Helen C. Kwok
(74) *Attorney, Agent, or Firm*—Vern Maine & Associates

(57) ABSTRACT

Acoustic sensing utilizing a bridge structure coupled about a portion of at least two sides of said bridge to a base substrate, wherein said bridge includes a piezoelectric section and has at least one active acoustic region proximate said bridge. A sensing material is disposed on at least a portion of at least one surface of the bridge, wherein the bridge produces stress effects measurable by an acoustic wave device located in the active acoustic region. According to one embodiment, the stress effects are measured by an acoustic wave device to sense a target matter. As target molecules accumulate on a sensing film affixed to at least a portion of the bridge, stress is produced in the bridge inducing a frequency change measured by an acoustic wave device.

21 Claims, 22 Drawing Sheets

U.S. PATENT DOCUMENTS

| | | | |
|---|---|---|---|
| 5,729,075 | A | 3/1998 | Strain |
| 5,821,402 | A | 10/1998 | Okajima et al. |
| 5,867,074 | A | 2/1999 | Ogiso et al. |
| 5,977,767 | A | 11/1999 | Chaparala |
| 6,257,048 | B1 * | 7/2001 | Hietala et al. ............... 73/24.01 |
| 6,335,667 | B1 | 1/2002 | Takagi et al. |
| 6,336,366 | B1 | 1/2002 | Thundat et al. |
| 6,378,370 | B1 | 4/2002 | Haskell et al. |
| 6,432,362 | B1 * | 8/2002 | Shinar et al. ............. 422/82.01 |
| 6,539,774 | B1 | 4/2003 | Zinck et al. |
| 6,553,836 | B2 | 4/2003 | Williams |
| 6,668,627 | B2 | 12/2003 | Lange et al. |
| 6,820,469 | B1 * | 11/2004 | Adkins et al. ............... 73/54.25 |
| 6,953,977 | B2 | 10/2005 | Mlcak et al. |
| 6,984,925 | B2 | 1/2006 | Morley et al. |
| 7,002,281 | B2 | 2/2006 | Andle |
| 7,129,806 | B2 | 10/2006 | Sato |
| 7,168,298 | B1 * | 1/2007 | Manginell et al. .......... 73/54.25 |
| 2003/0119220 | A1 * | 6/2003 | Mlcak et al. .................. 438/52 |
| 2005/0034542 | A1 | 2/2005 | Thaysen |
| 2005/0034822 | A1 | 2/2005 | Kim et al. |

FOREIGN PATENT DOCUMENTS

| | | |
|---|---|---|
| JP | 2075963 | 3/1990 |

OTHER PUBLICATIONS

Boy, J.J. et al., "Theoretical and Experimental Studies of the Force-Frequency Effect in BAW LGS and LGT Resonators", IEEE International Frequency Control Symposium and PDA Exhibition, 2001, pp. 223-226.

"Acoustic Wave Sensors", Nov. 9, 2006 [online] [retrieved on Nov. 9, 2006] Retrieved from the internet <URL://http://www.visensors.com/tech_ref/AWS_WebVersion.pdf>, pp. 1-44.

Tappura, Kirsi, "Biosensors", VTT Technical Research Centre of Finland; Apr. 2006, pp. 1-23.

Fletcher E.D. et al., "A Comparison of the Effects of Bending Moments on the Vibrations of AT and SC (or TTC) Cuts of Quartz", Proc. 33rd Annual Symposium on Frequency Control, 1979, pp. 346-350, Philips Research Laboratories, England.

Kazinczi, R. et al., "Adsorption-Induced Failure Modes of Thin-Film Resonators", Materials Research Society Symposium, 2002, 6 pages.

Thundat, T. et al., "Detection of Mercury Vapor Using Resonating Microcantilevers", Applied Physics Letters, Mar. 27, 1995, pp. 1695-1697, vol. 66, Issue 13.

Andle, J.C. et al., "Acoustic Wave Biosensors", Nov. 1995, pp. 1-22, Laboratory for Surface Science and Technology and Department of Electrical and Computer Engineering, University of Maine, Orono, Maine.

Lukaszek, T.J. et al., "Resonators for Severe Environments", 33rd Annual Symposium on Frequency Control, 1979, pp. 311-321.

Kim, Yoonkee et al., "Force-Frequency Effects of Y-Cut Langanite and Y-Cut Langatate", IEEE International Frequency Control Symposium and PDA Exhibition, 2002, pp. 328-332.

Kher, Unmesh, "Beyong the Sixth Sense", Jan. 4, 2004 [online] [retrieved on Nov. 19, 2007] Retrieved from the internet <URL:http://www.time.com/time/printout/0,8816,570260,00.html>.

* cited by examiner

HIGH SENSITIVITY ACOUSTIC WAVE MICROSENSORS BASED ON STRESS EFFECTS

RELATED APPLICATIONS

This application claims the benefit of U.S. Provisional Application No. 60/863,871, filed Nov. 1, 2006. This application is also related to pending U.S. Utility patent application Ser. No. 11/753,047, filed May 24, 2007, both of which are herein incorporated in their entirety by reference.

FIELD OF THE INVENTION

The invention relates to sensors, and more particularly, to sensing technology involving micromachined structures in piezoelectric acoustic wave devices.

BACKGROUND OF THE INVENTION

There have been significant advances in the sensing industry based on requirements for such fields as airport security as well as military and medical applications. For example, it is broadly publicized that the airport and ship terminal screening measures for explosives, radioactive or biological dangers have been hampered by inadequate sensing equipment.

There are various types of sensors and sensing applications. Current gas sensors are typically based on mass loading of a sensing film upon exposure to a target analyte. Mass loading refers to measuring changes of the vibrating member due to on an increase of the mass caused by an adsorption of some gas. A mass loaded resonator has electrodes and the device vibrates at some resonant frequency. As the gas molecules are adsorbed by the sensing film, the added mass of the gas molecules causes a change in the propagation or resonance of the acoustic wave device. For such a device the resulting change is a frequency decrease.

Another sensing area involves cantilevers. One cantilever method employs a highly sensitive cantilever structure with optical detection based on bending of the cantilever. A further cantilever technique is a piezoresistive/piezoelectric element on the cantilever that directly senses induced strain caused by bending of the cantilever as a resistance or voltage change. However, as detailed in U.S. Utility patent application Ser. No. 11/753,047 and reiterated herein, these prior systems fell far short of the customer requirements in the expanding array of sensing applications.

Some examples of the current art are described herein in general terms for illustrative purposes. Referring to FIG. 1A, which is a capacitance-based platform disposed in a package, typically a microelectromechanical system (MEMS) capacitive diaphragm sensor. Disposed upon the substrate 5, there is a lower plate 20 and a vented upper plate 10 with a central fill hole 25. A polymeric sensing film 30 is disposed between the lower plate 20 and the upper plate 10. Electrical connectivity is provided by the lower plate electrical connector 15 that allows the energy source and response measurement connections. Typically these devices use thick film polymer sensing films to form a sensor array. As known to those in the art, there is a change in the dielectric constant of polymers upon exposure, thereby allowing detection. In this capacitive sensor design, there generally is a consistent gap width between the plates and a good baseline. Such a system is typically low in power and there is no pre-concentrator.

FIG. 1B depicts a SiC resonator, which typically is constructed in a sensor array, and uses mass loading for detection. The piezoelectric low frequency MEMS structure in FIG. 1B illustrates a P-type silicon substrate 40 upon which is disposed an N-type material 45, such as SiC. Not only is the substrate 40 covered by the N-type material 45, but the N-type material 45 extends outwardly from an end of the substrate 40 creating an extended type structure which shall be termed a cantilevered beam. An epitaxial piezoelectric layer (AlN) 50 is disposed on portions of the N-type coating 45, including portions on the cantilevered beam. An upper electrode 55 is disposed upon the epitaxial piezoelectric layer 50. A lower electrode contact 35 is coupled to the N-type layer on a portion above the substrate 40 without extending onto the cantilevered beam. This structure may include a pre-concentrator to increase sensitivity, but takes further time to collect samples, such that they generally do not operate in real time. This typically uses thick film polymers and subject to polymer thickness control issues. The resonator is prone to Q and temperature stability issues since the polymer needs cover the actively vibrating area of the sensor. It is also not energy efficient with power spikes for required heating of the pre-concentrator. For illustrative purposes, a further description of this general type of device can be found in U.S. Pat. No. 6,953,977.

FIG. 2A illustrates a SAW delay line structure commonly used for sensing applications. This two port structure serves as a gas sensor by placing a gas specific sensing film 65 on the surface of the device in-between an input transducer 60 and an output transducer 70 which is disposed upon a piezoelectric SAW substrate 75. When the sensing film 65 gets exposed to a gas, mechanical and electrical perturbations of the sensing film 65 causes a corresponding change in the propagation characteristics of the acoustic wave device. When the SAW structure is coupled to an oscillator circuit, the changes result in an increase or decrease in oscillator frequency. Some examples of sensing films can be metal, metal oxide, metal nitride, polymer, or biological material (antigens, bacterial biofilms, or cell cultures). In certain combinations of films and device structures it is possible to extend the sensing film over the entire device or to employ the device conductors or substrate as the sensing medium. Again, the SAW sensor is prone to Q and temperature stability issues since the polymer needs cover the actively vibrating area of the sensor. Prior SAW resonators include those described in U.S. Pat. No. 6,335,667 and the multi-reflective acoustic wave devices as disclosed in U.S. Pat. No. 7,002,281.

The SAW-based platforms such as those illustrated in FIG. 2A typically have thick film polymers forming the sensor array. The sensing film is in the delay path and employs mass loading to detect change in frequency. A pre-concentrator can be used to increase sensitivity however the heating can cause high power spikes and is less energy efficient.

There are also known systems that measure the displacement of a cantilever using optics. Referring to FIG. 2B, a MEMS cantilever system with optical detection is depicted in which the mechanical resonance of a mechanical structure is employed. This type of system generally employs a silicon substrate which is not a piezoelectric material. The silicon substrate 80 has a cavity portion 100 and the structure includes layers about the periphery of the device, including a cantilever 85 extending from an end of the device. There is a sensing film 95 disposed upon a film surface 90 wherein the film surface 90 relates to attachment chemistry for disposing a sensing film 95, which is typically a metallization layer.

The silicon MEMS cantilever assembly 85 is typically coupled with a piezoelectric transducer (not shown) that is driven with an oscillator (not shown) to vibrate at the mechanical resonance of the cantilever 85. The laser diode 105 emits a laser beam signal 110 that reflects off the cantilever surface to the detector 115. The measured response can be used to lock that relative frequency and it can detect changes from that relative frequency.

Induced bending of the cantilever is in resonance mode and it uses a bi-cell detector 115 that measures the frequency and may also directly measure bending effects without a driving resonance for simplicity. This optical cantilever system measures the change of the angle of deflection of laser light 110 typically from a laser diode 105. The laser light 110 incident upon the end of the cantilever 85 typically bounces off the end of the cantilever and is received at an optical detector 115 such as a bi-cell optical detector. As gas affects the sensing film 95, there is a change to the cantilever 85, and the optical detection 115 measures changes to the angle of deflection of the laser light 110 bounced off the end of the cantilever 85. While complicated, the stress induced effects on the cantilever 85 combined with the optical detection provides satisfactory sensitivity.

In sum, sensors of this type typically measure changes in bending of the cantilever or changes in resonant frequency of the mechanical structure as defined by the cantilever geometry. In one approach, a change in the bending or strain of the sensing film translates into a direct change in the shape of the cantilever which is then measured by the optic detection system. Another approach uses changes in film mass or stiffness of sensing film to effect the overall spring mass constant of the cantilever altering its resonant frequency. In this resonance system, the cantilever needs a piezoelectric transducer and oscillator or electrostatic means to drive the unit in addition to the optical detection mechanism. Sensors of this type are controlled by the exact shape and resonant frequency of the cantilever itself, limiting the design and implementation and incurring direct damping of the cantilever resonant Q by the sensing film. For illustrative purposes, U.S. Pat. Nos. 5,719,324 and 5,445,008 describe background information for sensors of this type.

While sensing platforms are available, the industry demands a sensing technology that has a significant improvement in sensitivity and simplicity over existing sensing technologies.

SUMMARY OF THE INVENTION

The present invention according to one embodiment relates to sensing technology based on geometric response to film induced stress.

One embodiment of the invention includes a system for acoustic sensing, comprising a bridge structure coupled to a substrate about at least two sides of the bridge, wherein the bridge includes a piezoelectric section and has at least one acoustic wave device (AWD) proximate a portion of the bridge, the AWD includes an active acoustic region; and wherein a perturbation of the bridge produces stress effects measurable by the AWD.

Another embodiment of the invention further comprises a sensing material disposed on at least a portion of at least one surface of the bridge.

Yet another embodiment of the invention includes sensing material selected from at least one of the group consisting of: metal, metal oxide, metal nitride, ceramic, carbide, polymer, magnetic material, magnetostrictive material, electrostrictive material, and biological material.

A further embodiment of the invention includes an active acoustic region that is a thickness field excitation (TFE) structure formed by at least one positive electrode disposed on one side of the bridge and at least one ground electrode on an opposing side of the bridge, and wherein an electrical energy source is coupled to at least one positive electrode and at least one ground electrode.

Another embodiment of the invention includes a thickness field excitation (TFE) structure that is a two port device wherein a first transducer is electrically coupled to the electrical energy source by a positive electrical connection and a negative electrical connection and a second transducer provides a response related to an input electrical signal from the electrical energy source to a second positive electrical connection and second negative electrical connection.

One embodiment of the invention includes an active acoustic region that is a lateral field excitation (LFE) structure formed by at least one positive electrode and at least one negative electrode electrically coupled on one side of the bridge and to an electrical energy source.

Another embodiment of the invention includes an active acoustic region that is a surface generated acoustic wave (SGAW) structure formed by at least one transducer electrically coupled on one side of the bridge, wherein at least one transducer is electrically coupled to an electrical energy source.

Yet another embodiment of the invention further comprises a surface generated acoustic wave (SGAW) energy manipulating structure operatively coupled with at least one transducer, wherein the SGAW energy manipulating structure is selected from the group consisting of: reflective grating, delay line, metal trapping grating, multi-strip coupler, interdigital transducer, and thin film trapping layer.

A further embodiment of the invention includes a surface generated acoustic wave (SGAW) structure that is a one port device wherein a single transducer is electrically coupled to the electrical energy source by a positive electrical connection and a negative electrical connection.

Yet a further embodiment of the invention includes a surface generated acoustic wave (SGAW) structure that is a two port device wherein at least one transducer comprises a first transducer and a second transducer, wherein the first transducer is electrically coupled to the electrical energy source by a positive electrical connection and a negative electrical connection and the second transducer provides a response related to an input signal from the electrical energy source to a second positive electrical connection and second negative electrical connection.

Another embodiment of the invention includes a bridge that is a structure selected from at least one of the group consisting of: full bridge bulk acoustic wave, full bridge bulk acoustic wave monolithic crystal filter (MCF), full bridge bulk acoustic wave lateral field excitation (LFE), full bridge surface generated acoustic wave, full bridge film bulk acoustic resonator (FBAR), isolation bridge bulk acoustic wave, isolation bridge bulk acoustic wave MCF, isolation bridge bulk acoustic wave LFE, isolation bridge surface generated acoustic wave, and isolation bridge bulk acoustic wave FBAR, An additional embodiment of the invention includes a bridge that is coupled to the substrate by one of the group consisting of: two supports and four supports.

One embodiment of the invention further comprises a measurement device coupled to the acoustic wave device (AWD) and measuring the stress effects.

Another embodiment of the invention includes a method for detecting a target substance, comprising forming a piezoelectric bridge having at least one acoustic wave device disposed proximate a portion of the bridge; exposing the bridge to some environment; causing a stress response of the bridge from the environment; and detecting a response of the acoustic wave device to the bridge stress response.

Yet another embodiment of the invention further comprises disposing a sensing material on at least one portion of the bridge and allowing adsorption/absorption of the target substance by the sensing material.

An additional embodiment of the invention further comprises aligning the acoustic wave device at an angle ($\psi$) for a maximum change in frequency.

One embodiment of the invention includes a sensing device for measuring stress effects, comprising a substrate having electrical connections disposed about the substrate and providing connectivity to an electrical energy source and a measurement device; a bridge structure coupled to the substrate on a portion of at least two sides of the bridge comprising: at least one acoustic wave device formed proximate a portion of the bridge, the acoustic wave device comprising a piezoelectric section with at least two electrodes disposed thereon, wherein a perturbation of the bridge causes a change in electrical properties of the acoustic wave device, the change in electrical properties modifying a signal from the electrical energy source in a manner that is measurable by the measurement device.

Yet another embodiment of the invention further comprises a sensing material disposed on at least a portion of at least one surface of the bridge causing perturbation of the bridge.

In a further embodiment of the invention, the sensing device is selected from at least one of the group consisting of: bulk acoustic (BAW) bridge gas sensors, BAW bridge magnetic sensors, BAW bridge torque sensors, surface acoustic wave (SAW) bridge gas sensors, SAW bridge magnetic sensors, SAW bridge gas sensors, monolithic crystal filter (MCF) bridge gas sensors, MCF bridge magnetic sensors, MCF bridge torque sensors, film bulk acoustic resonator (FBAR) bridge gas sensors, FBAR magnetic sensors, and FBAR torque sensors.

In another embodiment of the invention, the piezoelectric section is selected from the group consisting of quartz, lithium niobate, lithium tantalate, langasite, aluminum phosphate, gallium phosphate, calcium-niobium-gallium-silicate, calcium-tantalum-gallium-silicate, strontium-niobium-gallium-silicate, strontium-tantalum-gallium-silicate, zinc oxide, aluminum nitride, and compositions thereof.

One embodiment of the invention includes a system for acoustic sensing, comprising: a bridge structure coupled to a substrate about a portion of at least two sides of the bridge, wherein the bridge includes a piezoelectric section and having at least one acoustic wave device (AWD) proximate a portion of the bridge, wherein the AWD includes an active acoustic region, wherein boundaries of the active acoustic region are decoupled from boundaries of the bridge; an electrical signal coupled to the bridge structure, wherein stresses induced in the bridge produce force-frequency effects measurable by the AWD; and wherein the force-frequency effects induce modulation of the electrical signal.

A further embodiment of the invention includes a sensing device for measuring physical parameters, comprising: a substrate having electrical connections disposed about the substrate and providing connectivity to an electrical energy source and a measurement device; a bridge coupled to the substrate on a portion of at least two sides of the bridge, the bridge comprising: at least one acoustic wave device formed proximate a portion of the bridge, the acoustic wave device comprising a piezoelectric section with at least two electrodes disposed thereon, wherein the bridge is responsive to stresses induced by application of a point force to the bridge, wherein the bridge stress response causes a change in electrical properties of the acoustic wave device, the change in electrical properties modifying a signal from the electrical energy source in a manner that is measurable by the measurement device.

One additional embodiment of the invention further comprises a diaphragm responsive to pressure disposed proximate the bridge, wherein the diaphragm transmits the point force.

Yet another embodiment of the invention includes magnetic fields acting upon a magnetic region proximate the bridge produce the point force.

A further embodiment of the invention includes an acceleration acting upon a proof mass proximate the bridge produces the point force.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

A fuller understanding of the invention can be gained from the following description when read with the accompanying drawings.

DETAILED DESCRIPTION

Figure 1A:
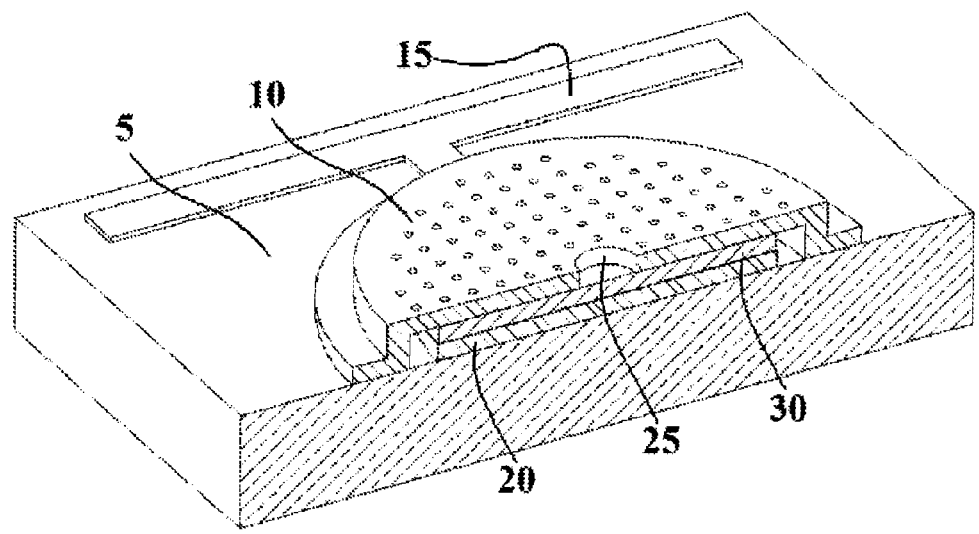
FIG. 1A is a prior art sensor for the capacitance-based platform.
Figure 1B:
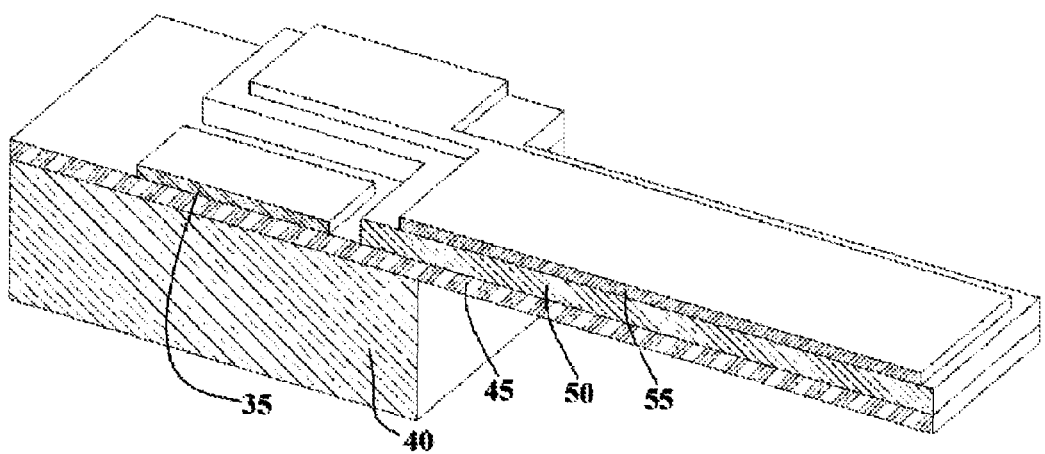
FIG. 1B is a prior art microelectromechanical (MEMS) resonator sensor.

A broad objective of the present invention is to improve sensitivity of sensor technologies by employing piezoelectric bridges wherein some of the improvements are based on the bridge's geometric response to film induced stress when exposed to a target substance.

The present application is related to the application entitled "High Sensitivity Microsensors based on Flexure Induced Frequency Effects" which describes the sensing technology employing cantilevers. While the cantilever embodiments detailed therein included multiple tethers of supports, the supports provide for some flexure of the cantilever. The sensors are taught to be designed so as to maximize the influence of flexural strain on the sensor response, typically through a strain dependent nonlinearity of the acoustic wave device using a measurand-induced stress to deform the freely suspended cantilever. In distinction, the stress-responsive microsensors embodiments detailed herein are intended to be more securely affixed such that some degree of stress is developed when the bridge is subjected to certain effects from the sensing films deployed on the bridge. In particular, the sensor structures are designed to maximize the influence of stress-induced nonlinear properties of the substrate on the electrical properties of a supported acoustic wave device. The supporting structures are designed to be well secured but to focus stress into the optimum directions.

The piezoelectric bridge in one embodiment utilizes the fact that the resonating active acoustic wave regions of the rigidly-fixed bridge will respond to the induced stress, caused by the increase or decrease in film stress when a sensing film along the length of the bridge is exposed to some influence such as a target gas. The sensing film will experience an increase or decrease in elastic properties causing the bridge to experience stress and this will, in turn, causes a corresponding change in frequency in the resonating portion(s) of the bridge, termed the active acoustic regions.

According to certain embodiments the bridges are held in place and are unable to move freely. As the sensing film undergoes changes, the bridge is subject to stress, and since the ends of the bridge are fixed, the bridge essentially builds up counter stress. The fixation of the bridges provides for an overall device that is less sensitive to vibration. Certain hostile environments are ideally suited for such a robust structure. However, it should be noted that the bridge sensing mechanism typically relies upon non-linear elastic properties and provides for $2^{nd}$ order effect ($3^{rd}$ order elastic constants) which may not be as large as the geometric changes associated with strain based sensors.

Background information about resonator forces and stress, including force frequency or flexure frequency with TSM devices, are detailed in the commonly assigned U.S. Pat. No. 6,984,925, entitled Low Acceleration Sensitivity Mounting Structures for Crystal Resonators and hereby incorporated by reference for all purposes. As is known, TSM devices are sensitive to force-frequency and force-flexure effects. The U.S. Pat. No. 6,984,925 according to one of the embodiments teaches orienting structures at optimal angles to minimize the effect of stress coupled to the device.

In one embodiment, stress within the bridge causes stress-induced frequency change in the AWD, e.g. a thickness shear mode (TSM) resonator/detector. In this embodiment, an internally-generated stress in the film induces the counter-stress of the bridge, causing non-linear material properties to change. As used herein, TSM devices include bulk acoustic wave (BAW) devices, lateral field excitation (LFE) devices, and monolithic crystal filter (MCF) devices. Other modes are generally allowed and analogous, including face shear modes, torsional modes, length extensional modes and thickness twist modes. For operation in air or vacuum the concepts and claims herein also apply to thickness extensional mode and should be considered to be inclusive. Surface generated acoustic wave (SGAW) devices include several specific classes, such as surface acoustic waves (SAW) devices, surface transverse waves (STW) devices, surface skimming bulk wave (SSBW) devices, pseudo-surface acoustic wave (PSAW) devices, Love wave devices, Lamb wave devices, and liquid guided acoustic wave (LGAW) devices, and Acoustic Plate Mode (APM). As used herein and unless limited elsewhere, acoustic wave device (AWD) shall be designated in a broad sense to include any such device that operates whether as a resonator, filter or delay line, and is not limited to a particular material, shape or cut.

A further embodiment of the present invention refers to using the bridge structure to monitor externally generated stress of the bridge, induced by "static" or "low frequency" magnetic fields. The magnetostrictive effect can be used with a sensing film or a proof mass with ferromagnetic properties may be employed to stress the bridge. A proof mass central to a bridge can induce a vertical bending and longitudinal stretching of the bridge in response to a magnetic field. The longitudinal stretching results in a restoring stress as a result of the elasticity of the bridge material.

Traditional lower frequency BAW devices (i.e. thickness shear mode (TSM) less than 20 MHz) suffer from two disadvantages when they are configured as mass loading sensors. The first disadvantage is the extremely low operating frequency. For acoustic wave sensors, a general rule of thumb is that the mass sensitivity is a function of frequency-squared. Thus, a 100 MHz TSM device will theoretically be 100 times more sensitive than a 10 MHz TSM device. This sensitivity increase is typically not realized since the frequency stability rapidly deteriorates with increased frequency when low-Q polymer films are placed in acoustically active locations. The direct measurement of the added mass through its effect on the resonant frequency is thus limited in practice and it is an object of this invention to allow a high frequency AWD to operate with optimized frequency stability (high Q) while still allowing the frequency to be perturbed by the sensing film-analyte interaction with optimized sensitivity.

Another disadvantage is that the change in frequency of the sensor is limited by the amount of mass that gets adsorbed onto or absorbed into the sensing film. Lower frequency TSM devices are generally large in size. The required amount of analyte scales at least as $1/F^2$ through area considerations above and beyond the $F^2$ sensitivity to mass per unit area. Like BAW devices, the disadvantage of the Surface Acoustic Wave (SAW) devices is that the change in frequency of the sensor will be limited by the amount of mass that gets adsorbed onto or absorbed into the sensing film.

It has also been shown that elastic film changes on non-acoustic wave cantilevers can create sensor platforms with much higher sensitivity than the same cantilever structures configured to respond to mass loading when exposed to a target gas. See for example, T. Thundat, E. A. Wachter, S. L. Sharp, R. J. Warmack, "*Detection of Mercury Vapor Using Resonating Microcantilevers*", Appl. Phys. Lett., 66, 13, 1995; and http://www.time.com/time/magazine/article/0,9171,570260,00.html. These structures again have the general limitations that the cantilevers themselves are the resonant structure, incurring manufacturing and environmental variability, and that the sensing film directly loads the acoustic wave, reducing Q and signal-to-noise ratio.

Force frequency effects are known in the art with respect to resonators. See for example, K. Yoonkee and A. Ballato, "Force-Frequency Effects of Y-cut Langanate and Y-cut Langasite", 2002 IEEE International Frequency Control Symposium and PDA Exhibition; and J. J. Boy, R. J. Besson, E. Bigler, R. Bourquinn, B. Dulmet, "Theoretical and Experimental Studies of the Force-Frequency Effects in BAW LGS and LGT Resonators", 2001 International Frequency Control Symposium and PDA Exhibition.

In one embodiment, the present invention uses the force-frequency effect of a film upon a bridge as measured by the acoustic wave device to sense the target matter, such as a gas, wherein the gas molecules accumulate on a sensing film affixed to at least a portion of the bridge.

By way of explanation, the sensing film is typically selected for a particular type of gas or gases, which may be sensitive to some gas(es) and not others. One example for detecting Hg, is the use of a Au film that picks up Hg and forms an amalgam. As the Hg is adsorbed on the Au sensing film, there exists an atomic density change of the gold film, causing the film to attempt to expand. The elasticity of the bridge material creates a restoring force (stress) that resists this expansion. The rate at which the Hg sticks to the surface changes the rate at which the BAW frequency changes. The amount of the Hg that sticks to the surface is concentration dependent and changes the magnitude of the response. Thus is can detect different concentrations of the sensed gas(es).

It should be noted that, as in the previously disclosed cantilevers, it is not necessarily the shape or dimension of the bridge that determines the operating frequency of the resonator. The bridge as a whole is not the resonating element and merely provides a rigid or semi-rigid support on which to introduce stress on the resonator (active acoustic region) such as a photolithographically defined trapped-energy resonator or delay line. The acoustic wave devices with their corresponding active wave regions reside on a portion of the bridge which is less than the dimensions of the entire bridge and lie within the edges of the bridge.

Figure 2A:
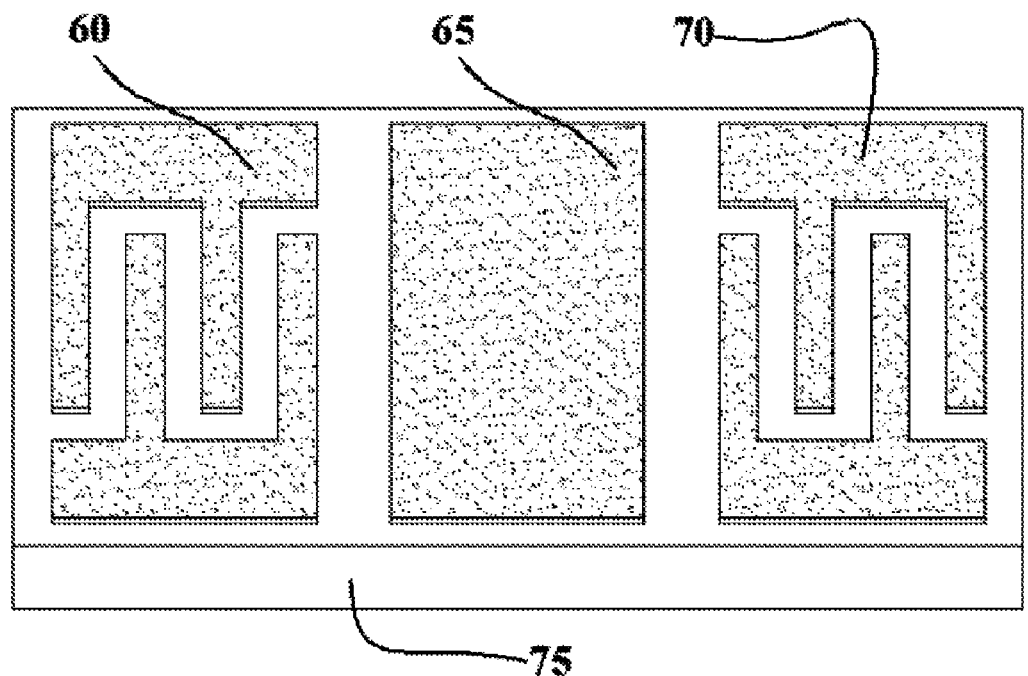
FIG. 2A is a prior art surface acoustic wave (SAW) delay line.
Figure 2B:
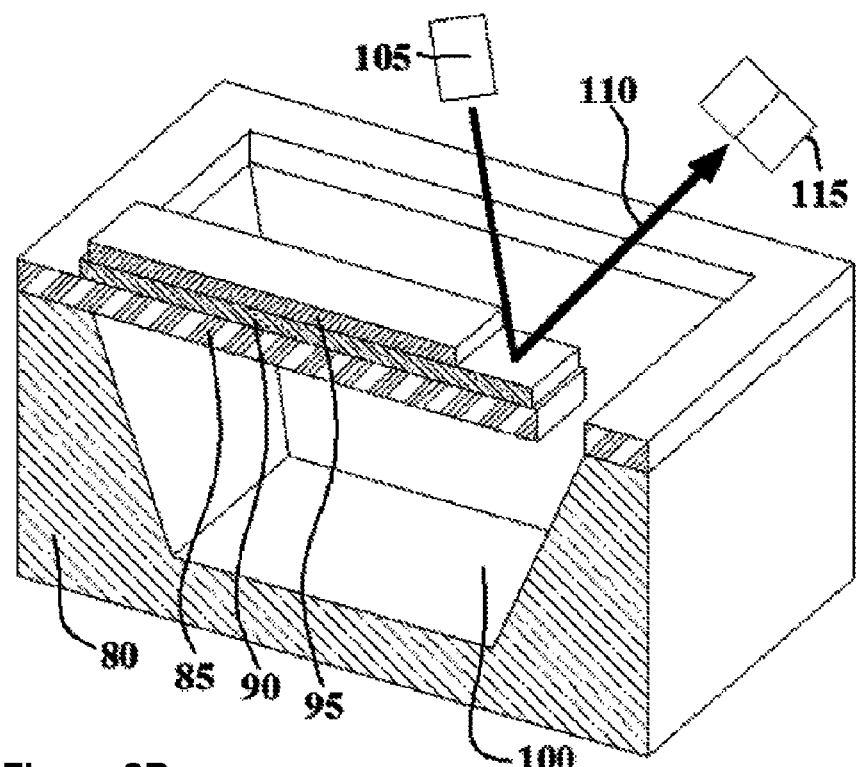
FIG. 2B is a prior art optical cantilever-based platform.
Figure 3A:
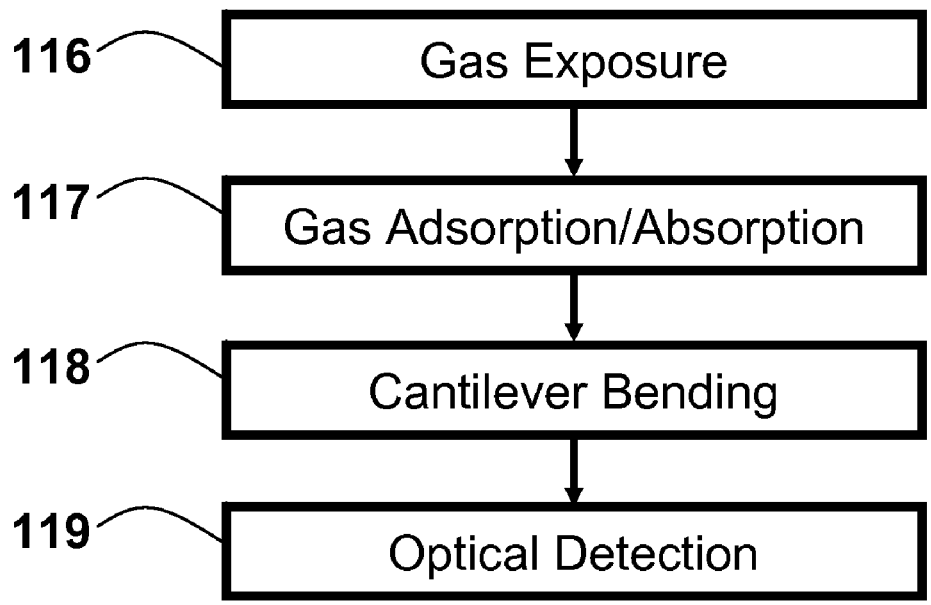
FIG. 3A is a prior art basic flowchart of the operation of an optical detection cantilever-based device.

Referring to FIG. 3A, the basic operation for a prior art MEMs optical cantilever based sensing platform described in FIG. 2B is presented. This example is a film stress based example that causes cantilever bending. In this gas sensing example, following the gas exposure 116, there is a polymer film adsorption 117. The adsorption of the gas with the sensing film causes the freely-supported cantilever to bend due to changes in the film stress. The cantilever bending 118 causes an impinging laser beam to deflect and allows for a highly sensitive measurement based on the optical detection 119.

The state of the art includes mechanical resonant frequency systems that are dependent on the mechanical geometry of the cantilever. For sensing applications, changes in a sensing film on the cantilever can cause changes in the spring constant of the mechanical cantilever causing the mechanical resonant frequency to increase or decrease depending on the type of sensing film response (i.e. mass loading versus elastic stiffening). One could envision bridge equivalent versions of this in which a resonant mode of the bridge (a micromachined "guitar string") serves as the resonator. Again, the sensing film would severely load the resonant bridge and the manufacturing variability of the bridges themselves is typically worse than that of trapped energy resonators or SGAW structures.

Typically, the mechanical resonant frequencies tend to be relatively low in frequency (i.e. <<100 kHz). Another known related effect is cantilever static bending. Static bending is not necessarily related to the cantilever mechanical resonant frequency, rather, the static bending is caused by a build up of film stress when the sensing film is exposed to a target gas. This stress causes the mechanical cantilever to bend in order to restore the equilibrium of force/stress and the amount of bending is measured optically. For reference purposes, U.S. Pat. No. 6,336,366 provides some additional background information.

Figure 3B:
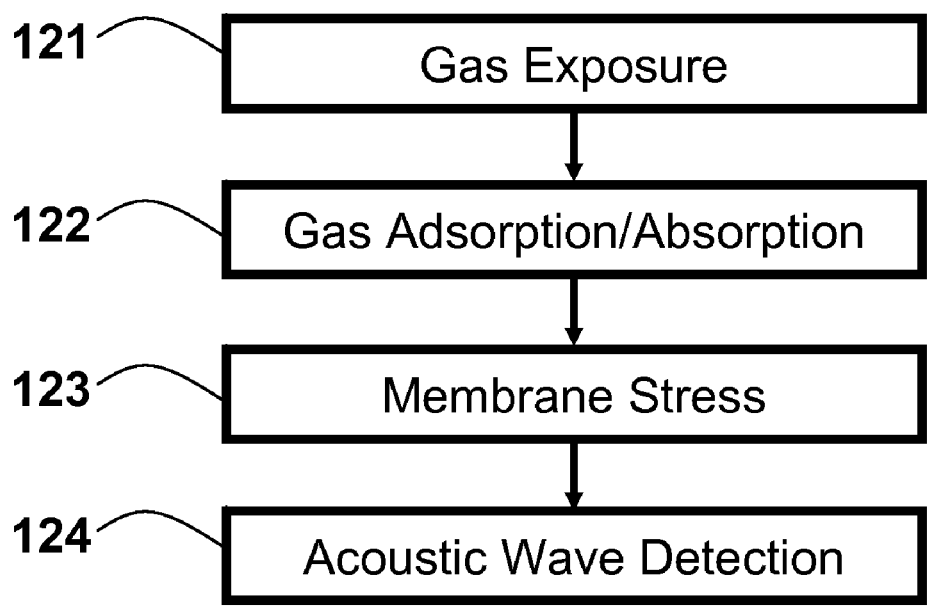
FIG. 3B is a basic flowchart of the operation of an acoustic wave detection cantilever-based device according to one embodiment.

With respect to FIG. 3B, one embodiment of the acoustic wave detection is shown. In this gas sensing embodiment, a bridge having one or more acoustic wave detectors with a sensing film is subject to gas exposure 121. There is some gas adsorption/absorption 122 which causes a membrane stress 123. This result is measured based on acoustic wave detection 124. By way of example, a frequency change due to the stress is measured and processed to determine the influence of the target substance. In practice there are numerous other measurands that can induce a stress either in a film or by acting on one or more materials affixed to or integrated with the bridge.

For acoustic wave devices in sensor applications, there are mechanical and electrical effects that cause changes. The mechanical effects typically include mass loading and elastic stiffening or softening. As a gas adsorbs onto or absorbs into the sensing film, it also changes the molar density, volume, or intrinsic stress of the film on the surface of the device, causing the retained bridge to build up a counter force. In one embodiment, the TSM device and the bridge are two separate elements wherein the film induced stresses in the bridge are focused onto the TSM sensor located at a bridge support. Typically, the TSM device detects the stress and responds with the force frequency effects.

For reference purposes, a cursory description of adsorption (mass loading) refers to the collection of a target material on the surface of a sensing material. When a sensing film gets exposed to a gas of interest, the gas molecules will either collect on the surface (adsorb) or diffuse into the bulk of the sensing film (absorb). The effect of adsorption usually only results in mass loading and the result is a decrease in piezoelectric resonant frequency of a piezoelectric (such as BAW, SGAW, FBAR, LFE) resonator structure. For delay line structures (i.e. SAW delay line), the surface collection of mass will cause a reduction in velocity of the wave as it propagates from input IDT through the sensing film to the output IDT (this decrease in velocity results in a change in phase). For the case of a non-piezoelectric mechanical cantilever, the adsorption (surface collection) effect is typically also mass loading and a decrease in mechanical resonant frequency results.

The effects of absorption (diffusion into the film) will cause a change in the molar density or the volume of the film due to expansion as the extra gas molecules diffuse into the bulk of the sensing film. This change in sensing film volume causes a build up of film stress that will generally cause the film to want to expand both vertically and horizontally. The vertical component has little effect on any of the structures; however, the horizontal component of film dimensional change causes three main effects, namely flexure, stiffening, and stress. The first effect, flexure, will occur on structures that are free to move in response to film expansion, as in U.S. Utility patent application Ser. No. 11/753,047, and the second effect, elastic stiffness, will typically occur on both cantilevers and clamped structures, while the third effect will occur mainly on clamped structures.

The flexure effect relates to absorption wherein the expansion of the film will cause all cantilevers to bend in response to the film stress and its need to equilibrate. After the cantilever stops bending, the result is a net zero stress across structure because the initial film stress equals the cantilever stress required to hold the cantilever in its final bent position. This bending is called flexure and the resultant effect is not stress but strain. There are notable distinctions between the acoustic wave case and the mechanical cantilever implementations, namely the mechanical cantilever bends and will cause a change in the shape of the cantilever and a large displacement of the vertical position of the end of the cantilever. In the prior art, the cantilever displacement is typically measured optically.

The acoustic wave resonance of the acoustic wave devices disposed upon the cantilevers are dependent on the piezoelectric thickness for BAW, the IDT and reflector design properties for SGAW, piezoelectric thickness for LFE and thickness/gap for MCF. The film stress applied to the cantilever and its supporting regions in the prior art causes a flexural deformation, said deformation causing a change in dimensions and potentially in material properties. The dimensional and material changes are reflected in the electrical response of the acoustic wave device. In particular, flexural deformation causes changes in the fundamental elastic, piezoelectric and dielectric constants that govern the electrical properties. This is readily seen by the significant differences between the dielectric constants of a ferroelectric or piezoelectric material measured at constant stress versus those measured at constant strain by way of nonlimiting example.

The absorption (diffusion into) of the film can cause the sensing film to increase in stiffness, appropriately called elastic stiffening effect. For the prior art cantilevers, the increase in film stiffness will cause an increase in the cantilever spring constant. This increase in spring constant causes the mechanical resonant frequency to increase. The mechanical cantilever spring constant changes and the mechanical resonant frequency increases. The sensitivity of this effect is less than the effect of measuring displacement of a bent cantilever.

Similarly, for acoustic wave devices, with or without etch relieved structures, this increase in film elasticity will cause an increase in the piezoelectric resonant frequency (for resonators) or an increase in velocity resulting in a change in phase for delay line structures. However this effect is small compared to the direct stress based changes of the acoustic wave devices. Since the film is, under conditions of light loading of the resonator, a mild perturbation, it stands to reason that small changes in film properties due to non-linear material effects will have less effect than the same effects in the main body of the resonator.

The acoustic wave resonance of the acoustic wave bridges are primarily dependent on the material properties and on the thickness for BAW, the IDT and reflector design properties for SGAW, piezoelectric thickness for LFE and thickness/gap for MCF. The increase in film stiffness causes an increase in resonant frequency (higher velocity for film) or change in phase for delay line (increased stiffness causes wave to travel faster). There is no dependence on the general shape of the bridge for well designed devices.

With respect to stress effects, the absorption (diffusion into) of the film causes stress of the sensing film since the cantilever is clamped and unable to increase in volume.

For acoustic wave devices in gas sensor applications, there are mechanical and electrical effects that cause changes. The mechanical effects include mass loading and elastic stiffening or softening. As gas adsorbs onto or absorbs into the sensing film, it also changes the intrinsic stress of the film on the surface of the device, causing the bridge to incur a counter stress. In one embodiment, the TSM device and the bridge are two separate elements. The bridge is stressed, transmitting stress into the TSM device, located at the support of the bridge. The TSM sensor detects the stress due to force frequency effects. This type of arrangement can be utilized for flow sensing where an impinging flow stream directed perpendicular to the bridge structure will cause either a direct bending and stretching of the bridge or cause the bridge to vibrate and thus modulate the frequency or phase of the AWD with the impinging signal such as a flow or vibration. For example, in one embodiment, the AWD has a frequency of operation and by stressing the membrane, it changes the frequency. If the membrane is vibrated, the associated AWD can be frequency modulated or phase modulated by the vibration. There are numerous applications for such a device such as vibration detection, magnetic sensing and communications.

According to one embodiment, the acoustic wave mode exists within a portion of that bridge structure defined by the acoustic wave device. The bridge structure itself uses a piezoelectric material and there is no need to apply a separate piezoelectric layer. Unlike the MEMS configuration detailed herein, the acoustic wave device operation is not necessarily dependent upon the sensing film or bridge spring constant. One embodiment of the invention observes the effects of the response which is the load applied to a resonator instead of changing the spring constant of the structure. According to one embodiment, the present invention does not change the fundamental operation but observes $2^{nd}$ order effects of the device.

According to one embodiment of the present invention, the piezoelectric resonant frequency or piezoelectric design frequency is not dependent upon the geometry of the bridge structures. These systems are dependent on other piezoelectric design criteria (i.e. BAW dependent on plate thickness and BAW electrodes, SAW dependent on IDT structure, MCF dependent on plate thickness and electrode structure) and as long as the bridge structure is of sufficient length and width to make a satisfactory piezoelectric resonator or delay line, the actual geometry of the bridge is not relevant in the processing. Thus, the acoustic wave device does not require any knowledge of the bridge. It only responds to mass directly on the active acoustic area or forces, stress, and strain in the vicinity of the acoustic active area that may be caused by the cantilever, bridge or other stress/strain causing structure.

There are several illustrative examples and embodiment for the various designs noted herein. In the BAW (TSM) resonator example, resonant frequency is typically determined by the plate thickness, top/bottom electrodes and overlap of top and bottom electrodes. Mass on the active area or stress or strain applied to the active acoustic area will result in a change in the resonant frequency.

For the MCF (TSM) Filter, design frequency may be determined by the plate thickness, the overlap of top input and ground, the overlap of top output and ground, and the gap in between the input and output electrodes. Mass over the active area or stress or strain applied to the active acoustic area will result in changes to the transmission of BAW energy from the input TSM to the output TSM.

Resonant frequency for the LFE (TSM) resonator is generally determined by the plate thickness, the input and output electrode, and the gap between the input and output electrode. Mass over the active area or stress or strain applied to the active acoustic area will result in changes to the resonant frequency of the LFE structure.

The FBAR is essentially a parallel plate resonator and is directly analogous to the TSM resonators detailed herein.

In the SAW resonator, the resonant frequency can be determined by the IDT periodicity/electrode structure, the grating (reflector) structure, and the effective cavity length. Mass over the active area or stress or strain applied to the active acoustic area will result in changes to the resonant frequency of the SAW structure.

The SAW delay line design frequency is typically dependent on the two-port IDT periodicity/electrode structure. Mass over the active area or stress or strain applied to the active acoustic area will result in a change in the transmission of SAW energy from the input IDT to the output IDT. The resonant frequency of the acoustic plate mode (APM) resonator is typically determined by the IDT periodicity/electrode structure, the grating (reflector) and the piezoelectric plate thickness. Mass over the active area or stress or strain applied to the active acoustic area will result in changes to the resonant frequency of the APM structure.

With respect to the FPW resonator, the resonant frequency is determined by the thin film piezoelectric thickness and the top and bottom electrode geometry. Mass over the active area or stress or strain applied to the active acoustic area will result in changes to the resonant frequency.

As noted herein, one of the embodiments of the present invention decouples the bridge from the AWD. As detailed herein, there are basically three modes of operation. The first mode, mass loading, generally results in a decrease in the resonant frequency. The second mode, elastic stiffening, is also related to the resonant frequency operations and more particularly to the increase in mechanical resonant frequency due to elastic stiffening. The third mode is related to a biasing stress of the bridge structure and its supports, and is the most sensitive as the detection operations are directly influenced by stress-induced changes of the substrate material. It should also be noted that for one or more AWDs, the response is not isolated to flexure only or stress only. In other words, according to one embodiment, the AWD can measure effects due to a combination of both stress and strain.

Figure 4A:
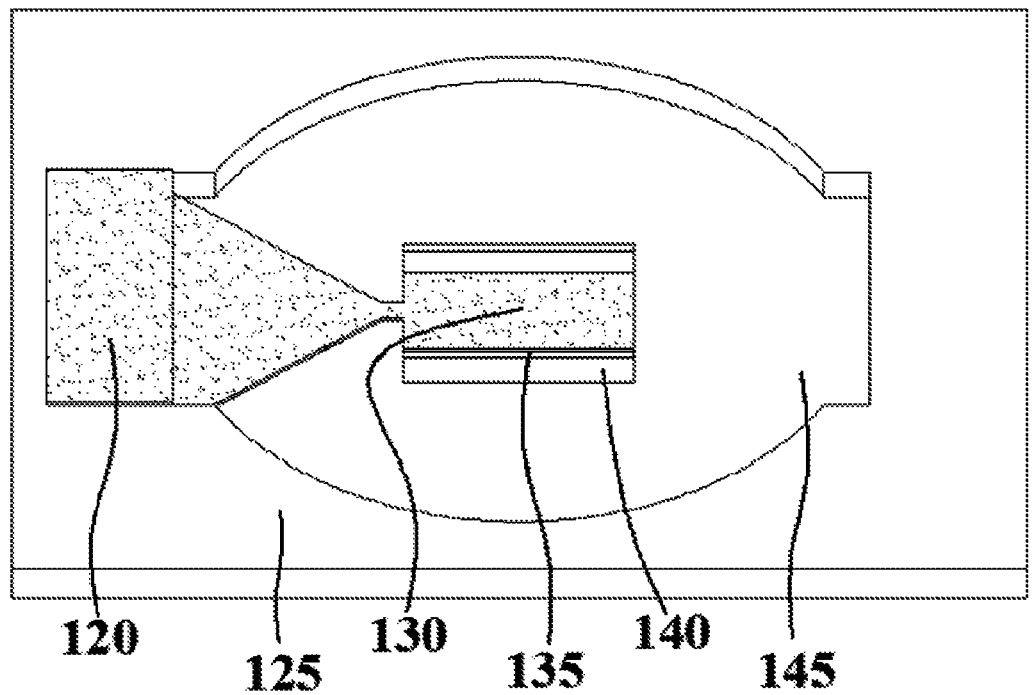
FIG. 4A is a top perspective view of a full bridge bulk acoustic wave (BAW) structure without a sensing film according to one embodiment of the present invention.
Figure 4B:
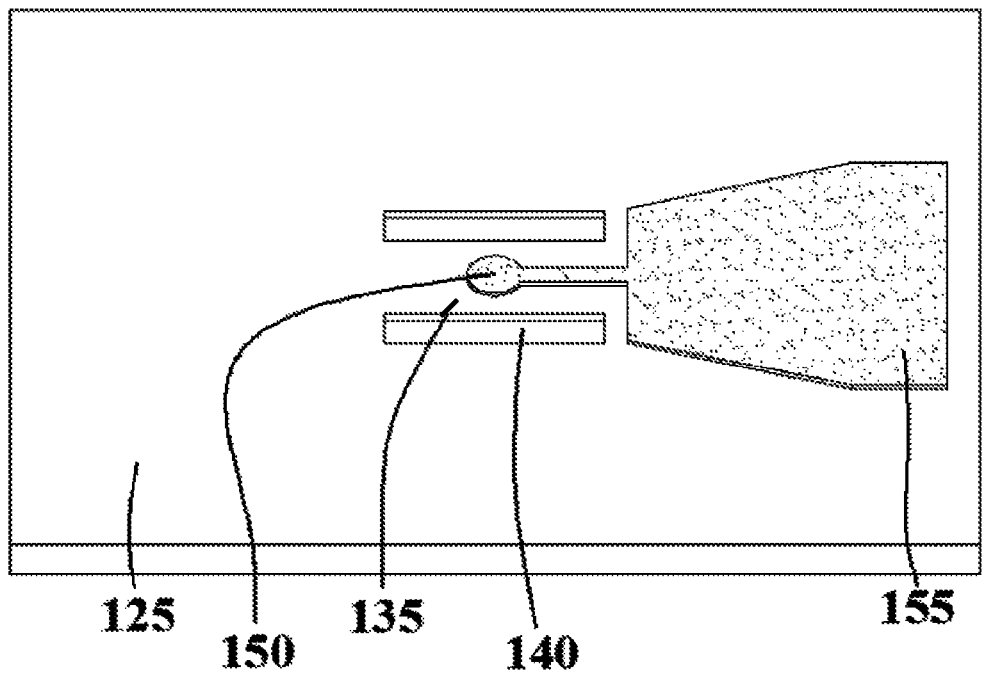
FIG. 4B is a bottom perspective view of the full bridge bulk acoustic wave (BAW) structure of FIG. 4A according to one embodiment of the present invention.
Figure 4C:
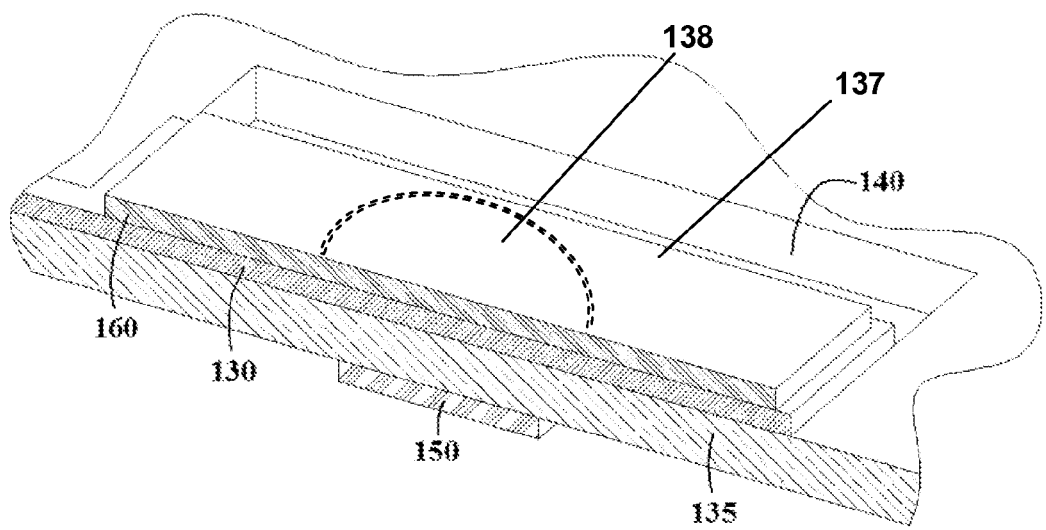
FIG. 4C shows a cut-away side perspective view of a full bridge bulk acoustic wave (BAW) structure according to one embodiment of the invention.

Referring to FIGS. 4A, 4B, and 4C a full bridge BAW structure is depicted. The structure substrate 125 is a piezoelectric material with a ground electrical connection 120 disposed thereon on one side and a positive electrical connection 155 on the opposing side. There is an etched pocket area 145 with a shape that depends upon the application and packaging considerations. An etched relief region 140 is proximate the acoustic wave bridge 137 and defines the peripheral side bounds of the bridge 137.

Within the acoustic wave bridge 137, an acoustic wave device (AWD) 138 is formed by the ground electrode 130 on one side of the piezoelectric bridge 135 and a positive electrode 150 on the other side, which in combination forms the acoustic wave device. The ground electrode 130 is coupled to the ground electrical connection 120 while the positive electrode 150 is coupled to the positive electrical connection 155. According to one embodiment, such an acoustic device operates in an active acoustic region proximate the overlay area of the electrodes 130, 150.

In this embodiment, the sensing film 160 is disposed on at least a portion of the ground electrode 130. The piezoelectric bridge 135 is attached to the piezoelectric substrate 125 with an etched relief 140 that helps in defining the side periphery of the bridge 137. The bridge 137 typically is dimensioned to provide proper support for the bridge with a degree of rigidity to allow for stress.

As the acoustic bridge 137 builds up a counter stress, the acoustic wave device responds by changing its frequency due to the stress being transferred into the piezoelectric bridge layer such as quartz. Thus in one embodiment, the structure forms a TSM device with the piezoelectric membrane 135 such that if it experiences stress due to the sensing film 160, the device responds to the stress by changing its frequency. The thickness shear mode device (TSM), in a general sense, thickness shear mode (TSM) refers to the effect that occurs when there is a piezoelectric material disposed between a ground electrode and a positive electrode on a device with properly selected substrate material and orientation such as AT quartz or Y-cut langasite. Application of a signal to the electrodes causes excitation of a thickness shear mechanical resonance. The intrinsic film stress of the sensing film induces flexure of the AWD. Depending on the details of the AWD, the resulting flexure may directly alter the AWD response or non-linear elasticity and density changes of the substrate may indirectly alter the AWD response during the induced flexure. Neither effect requires the sensing film to directly load the AWD's acoustic energy, although there is no specific prohibition. Thus, in one embodiment, no sensing film is required and in another the sensing film is not located in the acoustically active area 138.

For example, one mode of operation relates to force frequency effects due to gas adsorption by a film 160, wherein the frequency change will be related to the stress of the piezoelectric bridge membrane 135 due to film 160 elastic changes. The film 160 is shown on a substantial portion of the bridge 137. In other embodiments the film 160 can occupy a small portion of the bridge surface, all depending upon the design criteria. Multiple sensing films applied to a single bridge 137 are also within the scope of the invention.

Additionally, because the resonator portion (acoustic wave device) typically only responds to the stress coupled into the active acoustic area, it does not require a long bridge. If gas adsorption and resulting stress is linear with respect to gas concentration, frequency change of the acoustic wave device will be linear with respect to gas concentration. This particular design is well-suited for all kinds of sensing films (monolayer polymers, thin metal films, thin metal oxide films and others). Various biological and chemical responses can be measured using the present invention and the enhanced sensitivity provided therewith.

The bridge 135 can be any piezoelectric material such as quartz, as well as langasite and its isomorphs, and any illustrative examples employing quartz are not to be deemed limiting.

There are additional applications in relation to liquid sensing and physical sensing that are also within the scope of the invention. For example, instead of using a sensing film on the bridge, a magnetic film such as Nickel can be disposed on the end of bridge. The device can be placed in the presence of a magnetic field such that the magnetic field would influence movement of the bridge due to the magnetic coating. As an example, if you bias the device with a magnet in the presence of a gear tooth, it can measure speed. Such an example can be combined with a SAW or high frequency BAW in conjunction with a wireless transmitter thereby providing wireless magnetic sensing.

In one embodiment, the acoustic wave device is not centrally located with respect to the acoustic wave bridge 137. Multiple acoustic wave devices can be co-located about the bridge. The placement of the acoustic wave device in the single-ended embodiment can be at the bridge junction. In other embodiments, the acoustic wave device can be located along the bridge length depending upon the design criteria.

While the description references BAW devices, the present invention is applicable to various other such devices such as SAW, LFE, MCF, FBAR and MEMS type resonator devices.

For illustrative purposes, several examples of the bridge shape/design are described herein. The examples include two basic types, namely rectangular bridge and circular bridge. There are further subsets with rectangular whole and rectangular half and circular whole and circular half. And there are variations for each with different length and angles. The present invention can be configured in a variety of shapes and sizes depending upon the design criteria. The shape can be symmetrical and can also be asymmetrical, wherein the asymmetrical design can be used to tailor for stress effects. The use of rectangular and circular shapes is included to explain the teachings of the present invention and is not to be deemed limiting features. Other geometric shapes such as ovals, diamonds, and squares are all within the scope of the invention.

In one embodiment the acoustic wave device is a small section of the bridge. In another embodiment, nearly the entire bridge is the acoustic wave device, while allowing for energy trapping away from the edges of the bridge. There can also be multiple acoustic wave devices about the bridge depending upon the particular application and desired result.

Figure 5A:
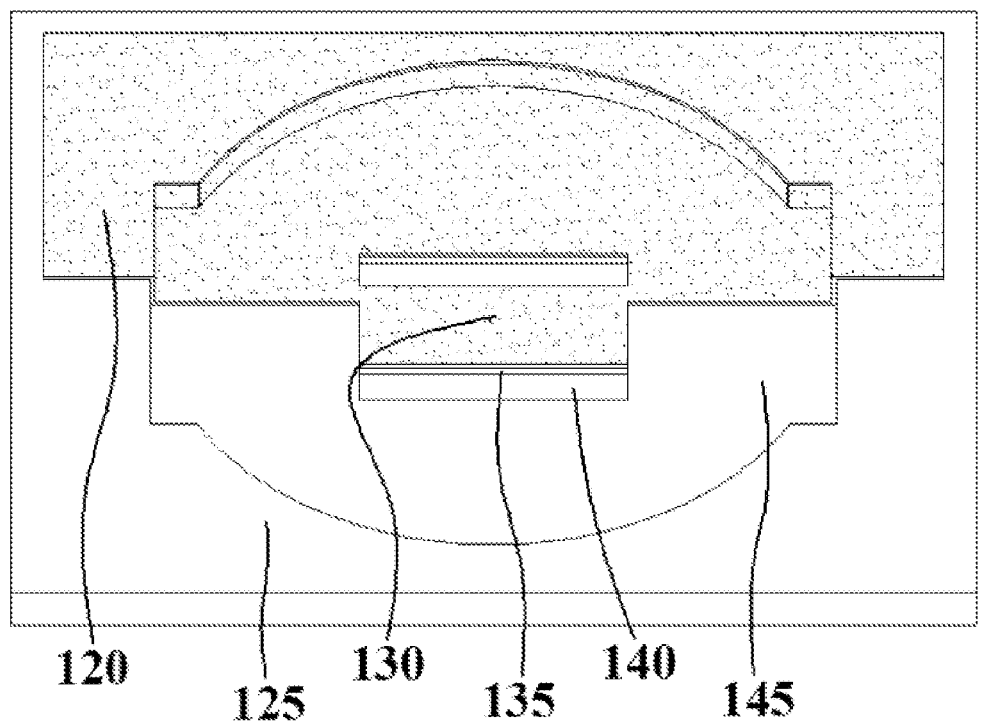
FIG. 5A is a top perspective view of a full bridge monolithic crystal filter (MCF) structure without a sensing film according to one embodiment of the present invention.
Figure 5B:
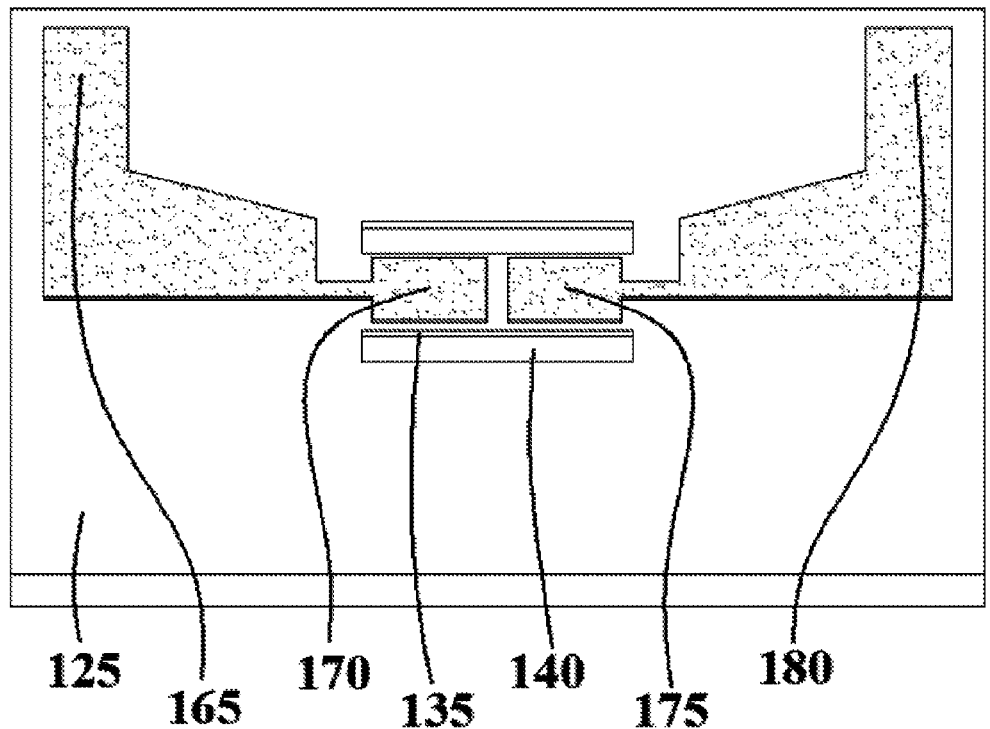
FIG. 5B is a bottom perspective view of the full bridge monolithic crystal filter (MCF) structure of FIG. 5A according to one embodiment of the present invention.
Figure 5C:
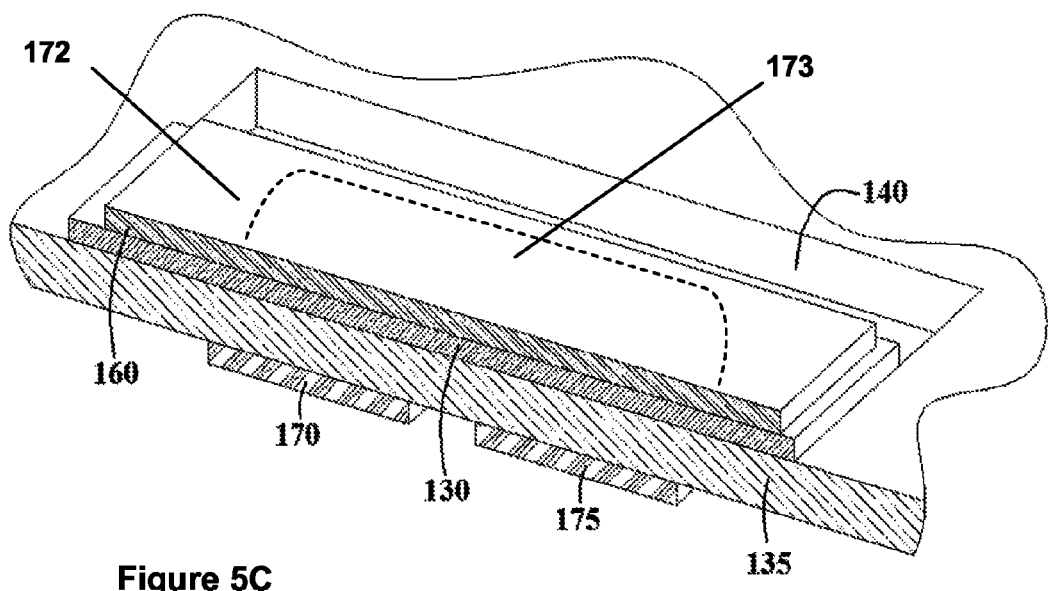
FIG. 5C shows a cut-away side perspective view of a full bridge monolithic crystal filter (MCF) structure according to one embodiment of the invention.

Referring to FIGS. 5A, 5B, and 5C, a two port acoustic wave device is depicted, such as a BAW monolithic crystal filter (MCF) device. On the piezoelectric substrate 125 there is a ground electrical connection 120 coupled to a ground electrode 130 on one side of the substrate 125. On the other side of the substrate 125 are at least two positive electrodes, namely an input positive electrode 170 and an output positive electrode 175.

In this embodiment, an input positive electrical connection 165 is disposed on the substrate 125 and electrically coupled to an input positive electrode 170 with the piezoelectric bridge 135 there between. This forms a first transducer or electrical port. There is also an output positive electrical connection 180 coupled to an output positive electrode 175 with the piezoelectric bridge 135 therebetween. This forms a second transducer or electrical port.

One skilled in the art will realize that the electrodes of an MCF can be disposed in numerous other sequences and that the ground electrodes can be split into separate input and output ground electrodes.

In operation, as the bridge 172 is subjected to stress caused by the film 160, it affects the coupling of the input to the output. The two port structure operates slightly different than a one port structure that only looks for frequency and loss changes. Employing the two port structure, one can look for frequency changes but by virtue of the two-pole coupled resonator structure there will be two frequencies wherein the two frequencies can be designed for various applications.

According to one embodiment the design can implement different levels of coupling between the electrodes, for situations such as overcoupled, undercoupled, and critically coupled operation. The two port structure allows measuring insertion loss by differentially measuring the signal at input/output and using a peak detector. The determination of whether the device operates in a particular mode depends upon whether the two electrodes are close enough for coupling effects. According to one embodiment, the stress of the bridge affects the properties of at least one of the transducers or the gap therebetween and therefore affects the coupling aspects. In other words, the device could be operating in a critically coupled mode and a change in the bridge might shift the resonances apart such that it becomes over-coupled.

Designs wherein the electrode spacing is initially large will result in both resonances being at the same frequency, yielding a Butterworth filter function. As the electrodes are strained into closer proximity the reactance of one resonator affects the other and the filter function presents two peaks in a Chebycheff filter function. The frequency spacing between these two frequencies is related to the intercoupling of the electrodes.

Figure 6A:
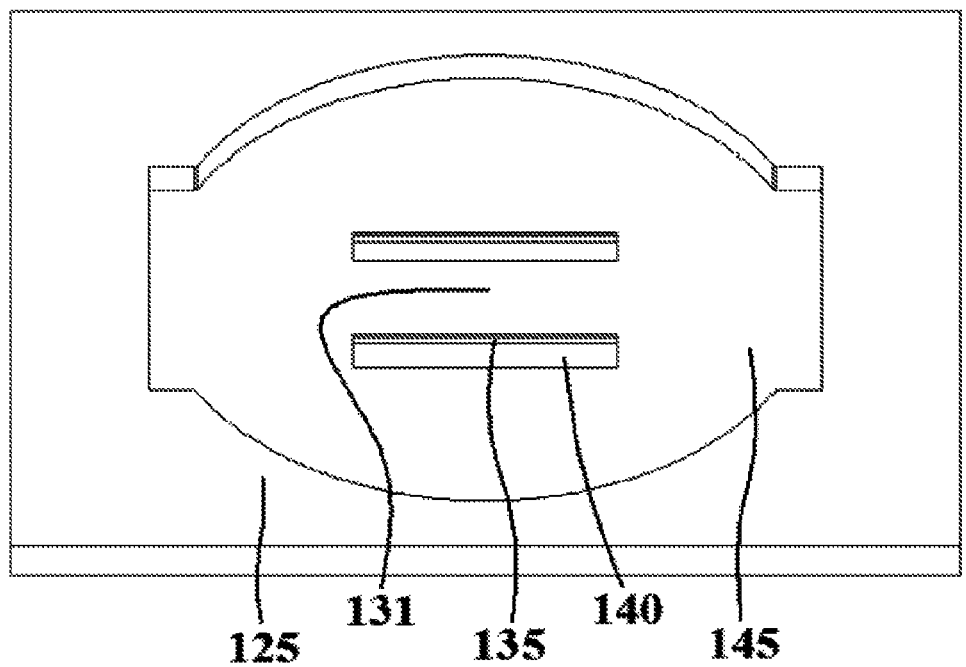
FIG. 6A is a top perspective view of an full bridge bulk acoustic wave (BAW) structure without a sensing film according to one embodiment of the present invention using lateral field excitation.
Figure 6B:
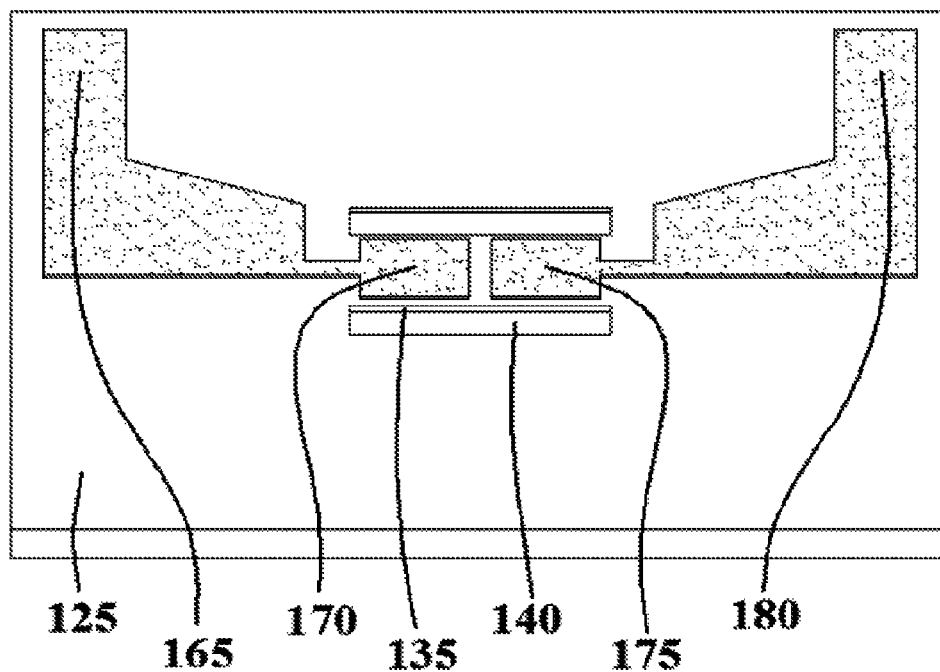
FIG. 6B is a bottom perspective view of the full bridge bulk acoustic wave (BAW) structure of FIG. 6A according to one embodiment of the present invention.
Figure 6C:
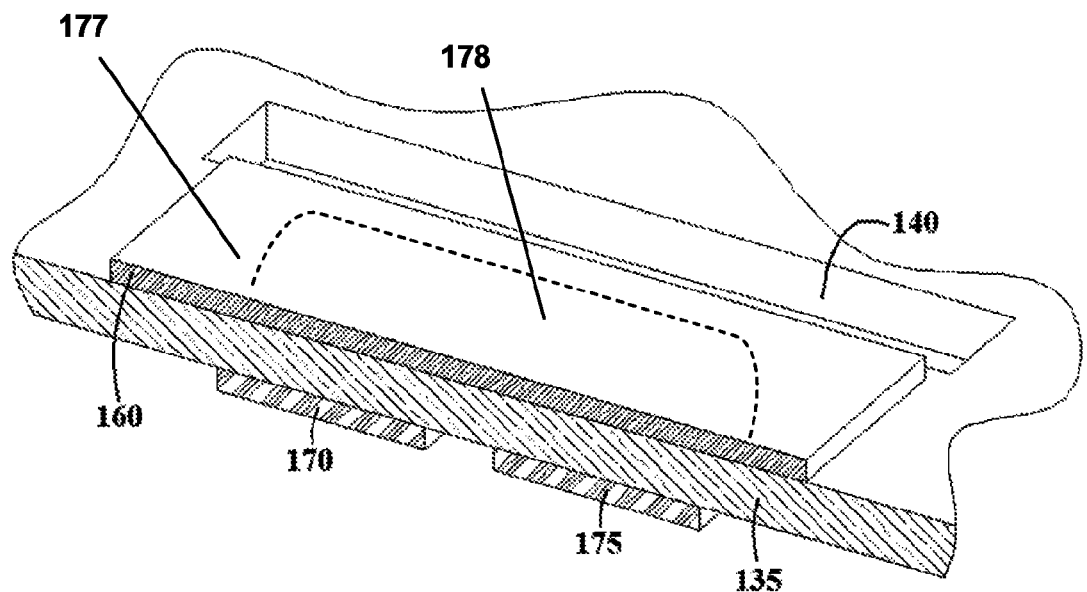
FIG. 6C shows a cut-away side perspective view of an full bridge bulk acoustic wave (BAW) structure according to one embodiment of the invention.

Referring to FIGS. 6A, 6B, and 6C, a full bridge bulk acoustic wave (BAW) lateral field excitation (LFE) structure is depicted. In this particular embodiment, the bridge 177 has no ground electrode. The sensing film 160 is disposed on the piezoelectric bridge 135. On the opposing side, there are the two electrodes, namely an input positive electrode 170 and an output positive electrode 175. This embodiment is not subject to thickness field excitation (TFE) which typically requires that there be electrodes on top and bottom so that the fields go through the device. Instead, this embodiment is subject to lateral field excitation (LFE) in which there is only electrodes on one side and the fields traverse the device laterally between the two electrodes 170, 175 on the same side. Certain material orientations allow a metal layer on the opposing surface with no influence upon the lateral field excitation and the addition of such films for other reasons is non-limiting.

Figure 7A:
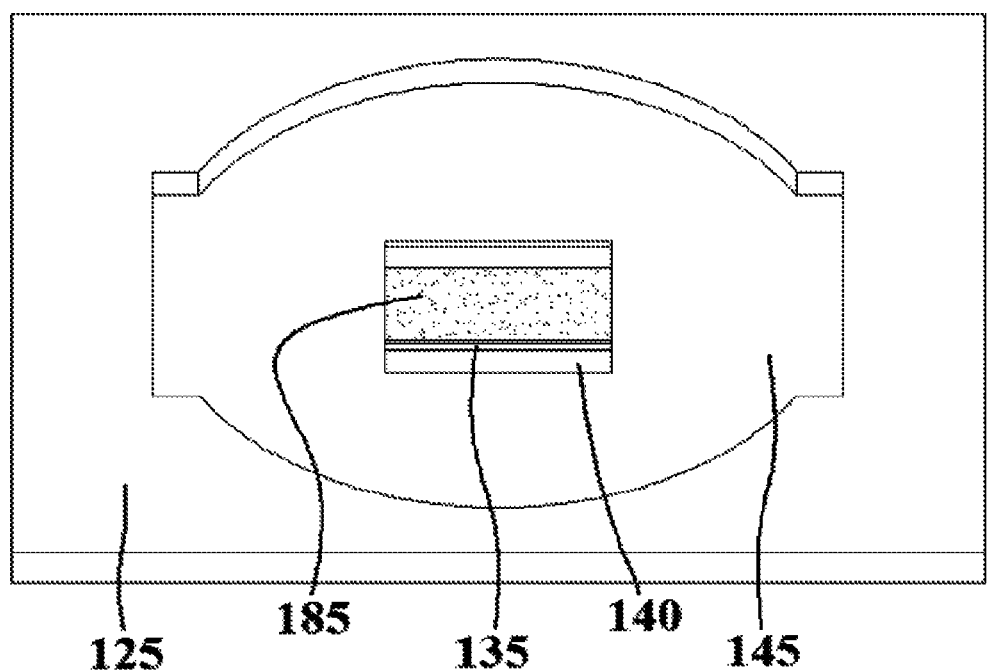
FIG. 7A is a top perspective view of a full bridge surface generated acoustic wave (SGAW) structure without a sensing film according to one embodiment of the present invention.
Figure 7B:
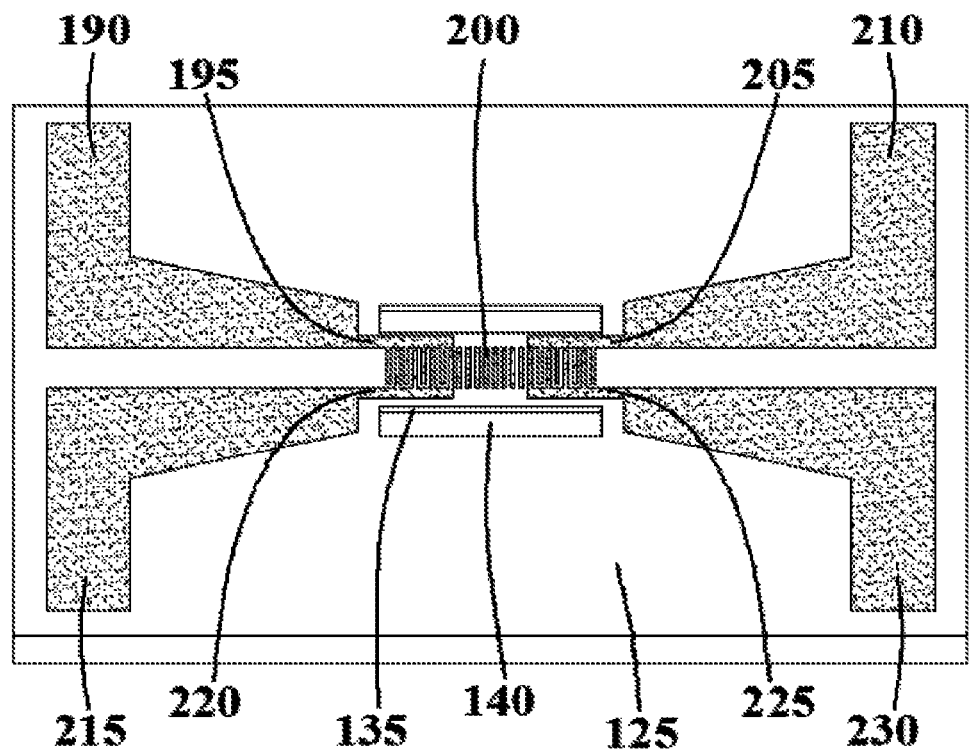
FIG. 7B is a bottom perspective view of the full bridge surface generated acoustic wave (SGAW) structure of FIG. 7A according to one embodiment of the present invention.
Figure 7C:
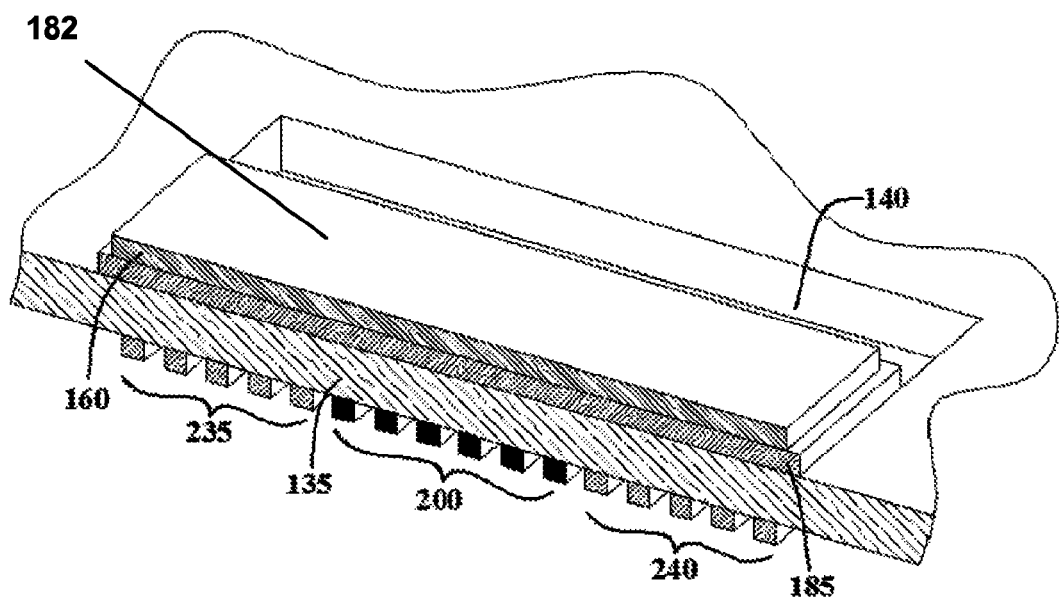
FIG. 7C shows a cut-away side perspective view of a full bridge surface generated acoustic wave (SGAW) structure according to one embodiment of the invention.

Referring to FIGS. 7A, 7B, and 7C, a full bridge surface generated acoustic wave (SGAW) structure on a bridge is depicted. According to one embodiment, the surface-launched acoustic wave devices employ some form of surface displacement in order to detect and quantify numerous measurands by means of perturbations induced in the electrical and mechanical properties of the devices by those measurands.

The surface generated acoustic wave devices basically include any such devices wherein transducers (one port or two port) are on the surface and input energy generates surface waves. Surface generated acoustic wave devices include several specific classes, such as surface acoustic waves (SAW), surface transverse waves (STW), surface skimming bulk waves (SSBW), pseudo-surface acoustic waves (PSAW), acoustic plate modes (APM), Love waves, Lamb waves, and liquid guided acoustic waves (LGAW), and Acoustic Plate Mode (APM). The surface displacement mediums include, for example, reflective gratings, metal trapping gratings, delay lines, and thin film trapping layers.

Referring again to FIGS. 7A, 7B, and 7C, the bridge 182 has a metalized surface 185 which is typically floating although it can be considered a ground plane. For example, the metalized surface 185 can be 'grounded' in certain ways such as with uniphase transducers. The acoustic wave bridge 182 is formed with etched relief section 140 on opposing sides of the bridge 182 wherein the bridge 182 is coupled firmly to the substrate 125.

There is an input positive port electrical connection 190 coupled to the input positive bus bar 195. On the other side there is input negative electrical connection 215 that is coupled to an input negative bus bar 220. An input interdigital transducer (IDT) 235 is electrically coupled to the input positive bus bar 195 and the input negative bus bar 220. One or more surface gratings are disposed on the bridge 182 wherein the input interdigital transducer (IDT) 235 receives energy from some acoustic energy source. There can be some form of surface displacement such as a central grating 200 that is placed in between the two IDTs 235, 240. The center grating 200 does not need to have the same number of fingers or the same grating period as the IDTs 235, 240.

On the output side, the output positive bus bar 205 is coupled to the output positive electrical connection 210. Similarly, the output negative bus bar 225 is coupled to the output negative electrical connection 230.

According to one embodiment, the stress can be measured across the SGAW by placing the SGAW propagation direction perpendicular to the length of the bridge. Furthermore, the propagation characteristics may be more sensitive to stresses applied at different angles with respect to the propagation direction and/or the crystalline axes, wherein the bridge length is defined at some angle such that the device properties determine an optimal angle as compared to the propagation direction.

An alternate embodiment employs a one port IDT that serves as both the input IDT and the output IDT with a pair of end gratings providing the reflections. Other embodiments include dispersive, non-dispersive, resonant, and delay line structures. On the surface transducer side, the acoustic waves are generated and measured using interdigital transducers (IDTs) disposed on the bridge 182. A SAW implementation may have an input IDT and an output IDT with a delay line therebetween. A STW implementation may have an input and out transducer with a metal trapping grating. A Love Mode device can use thin film trapping layers. A shear-horizontal APM may include input and output transducers interacting with surface displacements such that there is both a thickness shear mode device combined with a surface generated acoustic wave device such that the acoustic wave interacts with both surface of the plate for sensing.

According to one embodiment the piezoelectric bridge 135 can be materials such as quartz, lithium niobate, and lithium tantalite, wherein an electric potential is converted into a mechanical energy and vice versa. The specific geometry of the substrate and interdigital transducers and the type and crystallographic orientation of the substrate material determine the spectrum of waves that are excited and measured. In other embodiments the material employed to convert between electrical and mechanical signals may be any other piezoelectric material, ferroelectric material, or poled ceramic and the like, collectively referred to as piezoelectric for simplicity of presentation and definition.

In embodiments, polymer films are disposed on the bridge surface opposite the SAW transducer. Such films will not damp the SAW but will couple film stress into the bridge; altering the SAW properties.

Figure 8A:
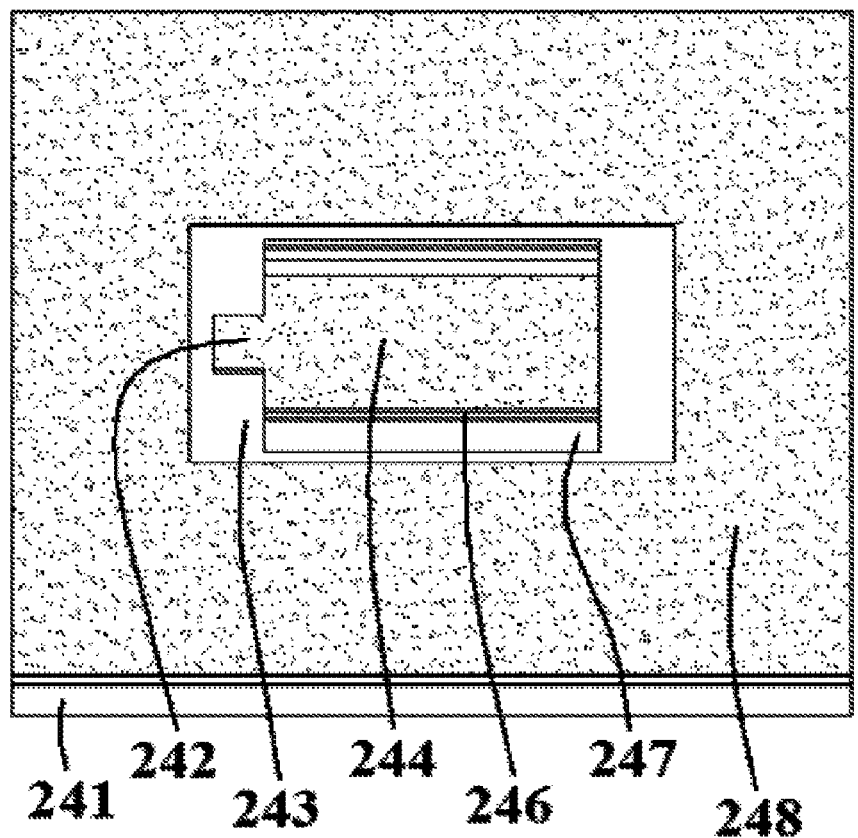
FIG. 8A is a top perspective view of a full bridge bulk acoustic wave (BAW) film bulk acoustic resonator (FBAR) structure without a sensing film according to one embodiment of the present invention.
Figure 8B:
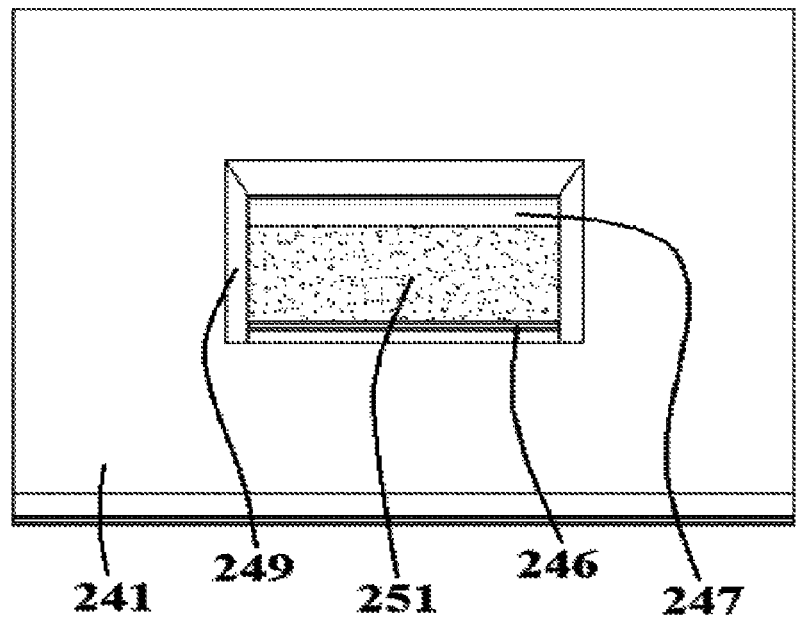
FIG. 8B is a bottom perspective view of the full bridge bulk acoustic wave (BAW) film bulk acoustic resonator (FBAR) structure of FIG. 8A according to one embodiment of the present invention.
Figure 8C:
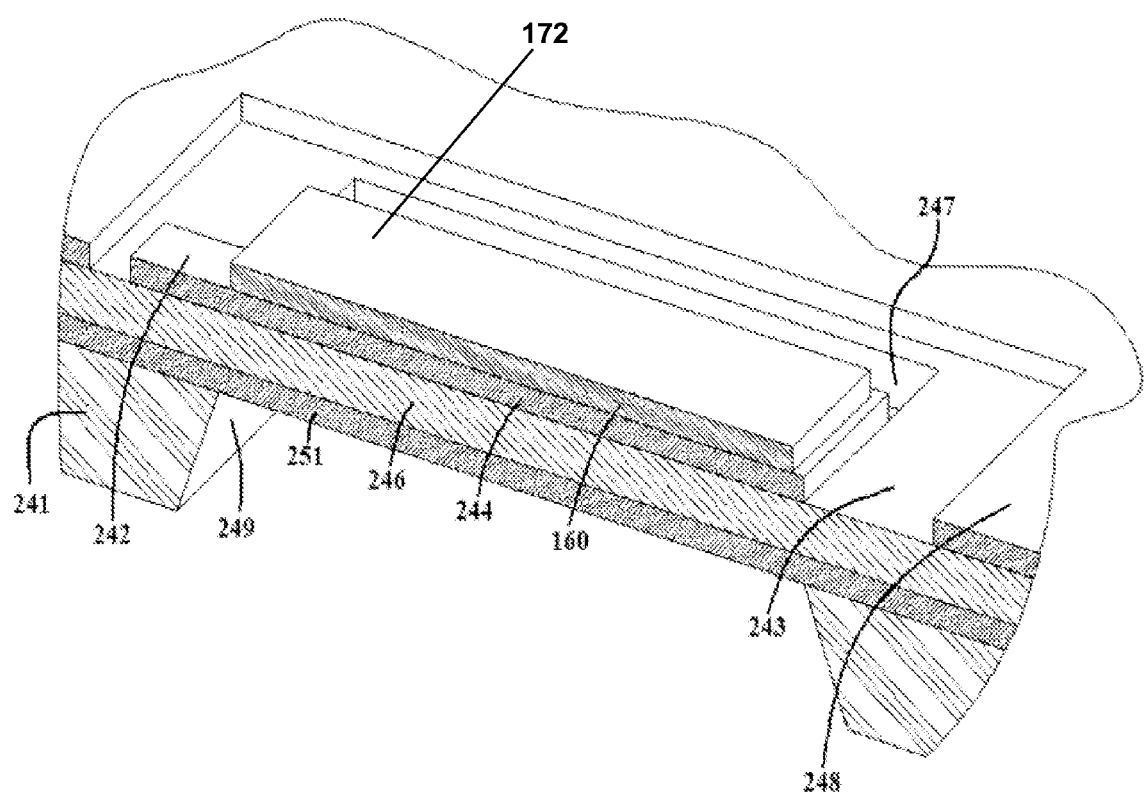
FIG. 8C shows a cut-away side perspective view of a full bridge bulk acoustic wave (BAW) film bulk acoustic resonator (FBAR) structure according to one embodiment of the invention.

Referring to FIGS. 8A, 8B, and 8C, a full bridge film bulk acoustic resonator (FBAR) is shown. The ground electrode 251 on one side of the bridge 172 is electrically coupled to a ground connection 248 typically by using vias (not shown) through the thin film piezoelectric layer 243. In this embodiment, a positive electrical connection 242 is disposed on the thin film piezoelectric layer 243 and electrically coupled to a positive electrode 244 with the FBAR piezoelectric bridge section 246 disposed beneath. The FBAR relief 247 defines the perimeter of the rectangular bridge structure 172 and the FBAR piezoelectric rectangular bridge 246 separates the positive electrode 244 and the ground electrode 251. The positive electrode 244 is preferably inset from the edges of the bridge to define an energy trapping region. A base substrate pocket 249 allows the bridge structure 172 to be suspended over an open area and coupled to the bridge ends for the firm support.

The bridge structure 172 of FIG. 8C illustrates one embodiment for the structure. The structure itself has a base substrate 241 with a base substrate pocket 249 defining the open area under the bridge 172. The ground electrode is 251 disposed on at least a portion of the base substrate and a portion of the ground electrode 251 is exposed to the open area of the pocket 249. On top of the ground electrode 251 is a thin film piezoelectric 243 covers at least a portion of the ground electrode 251. Substantially all of the thin film piezoelectric 243 is covered by a ground electrical connection 248 with the exception of the bridge section wherein there is a region without the ground electrical connection layer 248.

In the bridge section, the thin film piezoelectric is termed the bridge piezoelectric 246. The lower level of the bridge 172 is formed by the ground electrode 251 suspended over the base substrate pocket 249. The thin film piezoelectric bridge 246 is disposed over the ground electrode 251. A portion of the positive electrical connection 242 is disposed on the piezoelectric bridge 246 and the sensing film 160 is disposed upon the positive electrical connection 242. In the bridge region which is devoid of the ground electrical connection 248, there are FBAR relief structures 247 on the sides of the bridge 172.

The FBAR can operate with Thickness Field Excitation (TFE) which uses a z-directed electric field to generate z-propagating longitudinal or compressive wave. In a Lateral Field Excitation (LFE) FBAR, the applied electric field is in y-direction, and the shear acoustic wave (excited by the lateral electric field) propagates in z-direction.

Figure 9A:
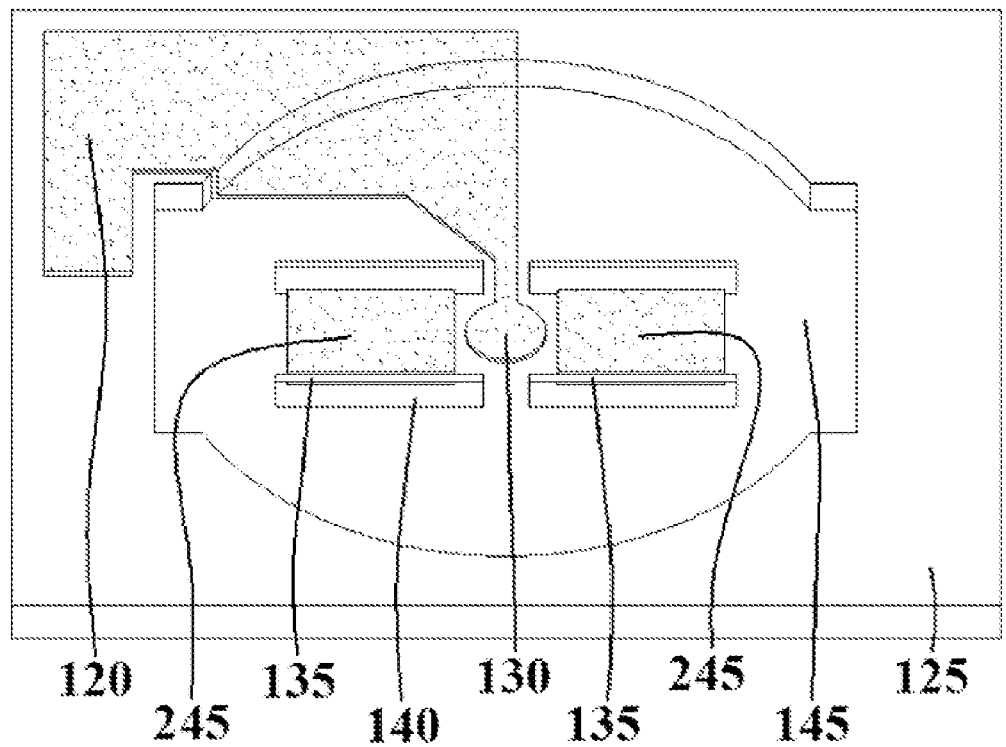
FIG. 9A is a top perspective view of an isolation bridge bulk acoustic wave (BAW) structure with a sensing film according to one embodiment of the present invention.
Figure 9B:
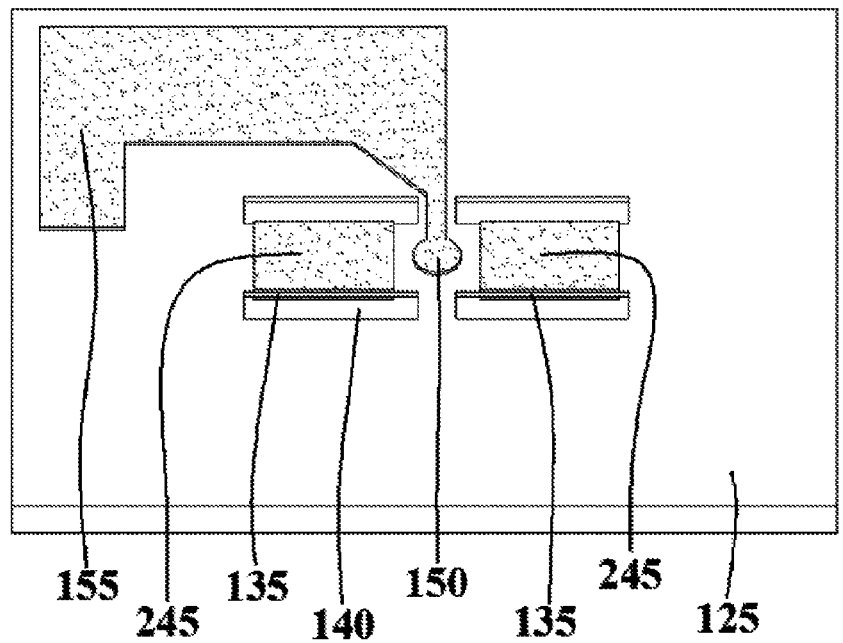
FIG. 9B is a bottom perspective view of the isolation bridge bulk acoustic wave (BAW) structure of FIG. 9A according to one embodiment of the present invention.
Figure 9C:
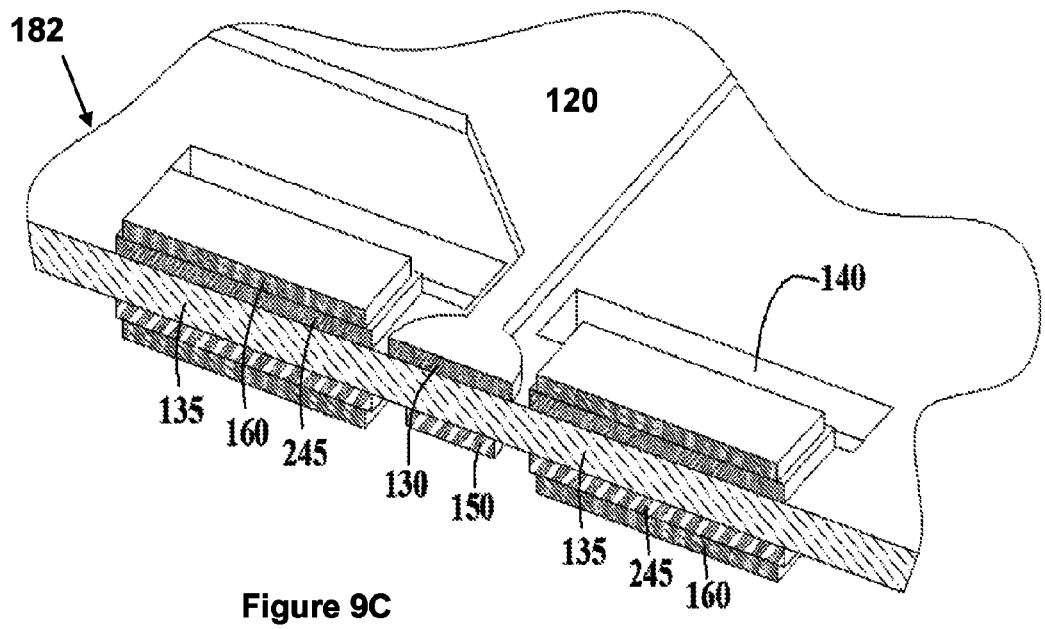
FIG. 9C shows a cut-away side perspective view of an isolation bridge bulk acoustic wave (BAW) structure according to one embodiment of the invention.

Referring to FIGS. 9A, 9B, and 9C an isolation bridge BAW structure is depicted according to one embodiment and illustrating multiple sections of sensing films. Unlike the full bridge structure in FIGS. 4a-4c, this embodiment forms an isolated bridge 182 with separate sensing films. The structure substrate 125 is a piezoelectric material with a ground electrical connection 120 disposed thereon on one side and a positive electrode 150 on the opposing side. There is an etched pocket area 145 with a shape that depends upon the application and packaging considerations. An etched relief region 140 is proximate the isolated acoustic wave bridge 182 and defines the peripheral side bounds.

The ground electrode 130 is coupled to the ground electrical connection 120 while the positive electrode 150 is coupled to the positive electrical connection 155. It should be noted that the active acoustic area is the overlapping region of the acoustic wave device. The sensing film 160 is disposed on at least a portion of the ground electrode 130. In this embodiment, the piezoelectric bridge 135 is attached to the piezoelectric substrate 125 with an etched relief 140 that defines the side periphery of the acoustic wave bridge 182. The bridge 182 typically is dimensioned to include proper support with a degree of rigidity to allow for the development of the stress.

Within the isolated acoustic wave bridge 182, an acoustic wave device in is formed by the ground electrode 130 on one side of the piezoelectric bridge 135 and a positive electrode 150 on the other side, which in combination forms the acoustic wave device (AWD). According to one embodiment, such an acoustic device operates in an active acoustic region proximate the overlay area of the electrodes.

As the acoustic bridge 182 builds up a counter stress in each arm, the acoustic wave device responds by changing its frequency due to the stress being transferred into the piezoelectric bridge layer 135 such as quartz. Thus in one embodiment, the structure forms a TSM device with the piezoelectric membrane 135 such that if it experiences stress due to the sensing film 160, the device responds to the stress by changing its frequency.

For example, one mode of operation relates to stress force frequency effects due to gas adsorption by a film 160, wherein the frequency change will be related to the stress of the acoustic wave bridge 182 due to film 160 structural and chemical changes and the stresses coupled therefrom into the piezoelectric bridge. In this embodiment the film 160 is shown on multiple sections of the bridge 182. Multiple sensing films 160 applied to a single bridge 182 allow for detection of different target substances. Alternatively, the sensing films 160 can be oriented for maximum response and sensitivity for a particular target substance.

Additionally, because the resonator portion (acoustic wave bridge device) typically only responds to the stress coupled into the active acoustic area, it does not require a long bridge. If gas adsorption and resulting stress is linear with respect to gas concentration, frequency change of the acoustic wave device will be linear with respect to gas concentration. This particular design is well-suited for all kinds of sensing films (monolayer polymers, thin metal films, thin metal oxide films and others). Various biological and chemical responses can be measured using the present invention and the enhanced sensitivity provided therewith.

The bridge of the present invention can be configured in a variety of shapes and sizes depending upon the design criteria. The shape can be symmetrical and can also be asymmetrical, wherein the asymmetrical design can be used to tailor for stress effects. The use of rectangular shapes is included to explain the teachings of the present invention and is not to be deemed a limiting feature. Other geometric shapes such as ovals, diamonds, and squares are all within the scope of the invention.

In one embodiment the formed acoustic wave device is a small section of the bridge. In another embodiment, nearly the entire bridge is the acoustic wave device. There can also be multiple acoustic wave devices about the bridge depending upon the particular application and desired result.

One aspect of the isolation bridge is that it allows for coupling of the stress into the resonator but separating the sensing film from the active acoustic areas. Such isolation makes the inclusion of sensing films on multiple sides of the bridge easier to process. Another application of the isolation relates to the use of very thick polymer films that allows for coupling stress from outside the device that would otherwise damp the results.

Figure 10A:
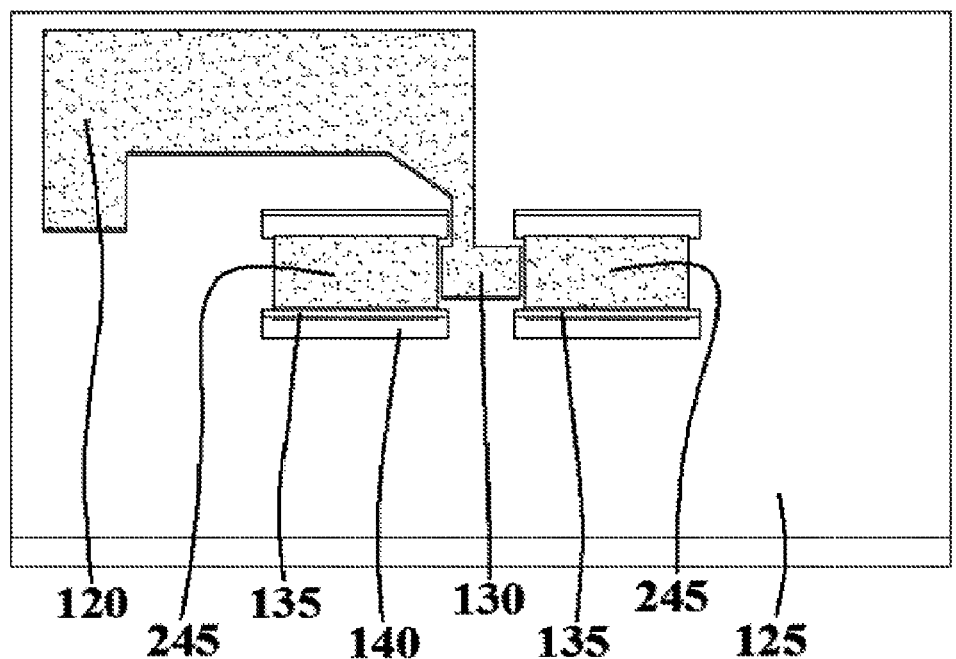
FIG. 10A is a top perspective view of an isolation bridge bulk acoustic wave (BAW) monolithic crystal filter (MCF) structure with a sensing film according to one embodiment of the present invention.
Figure 10B:
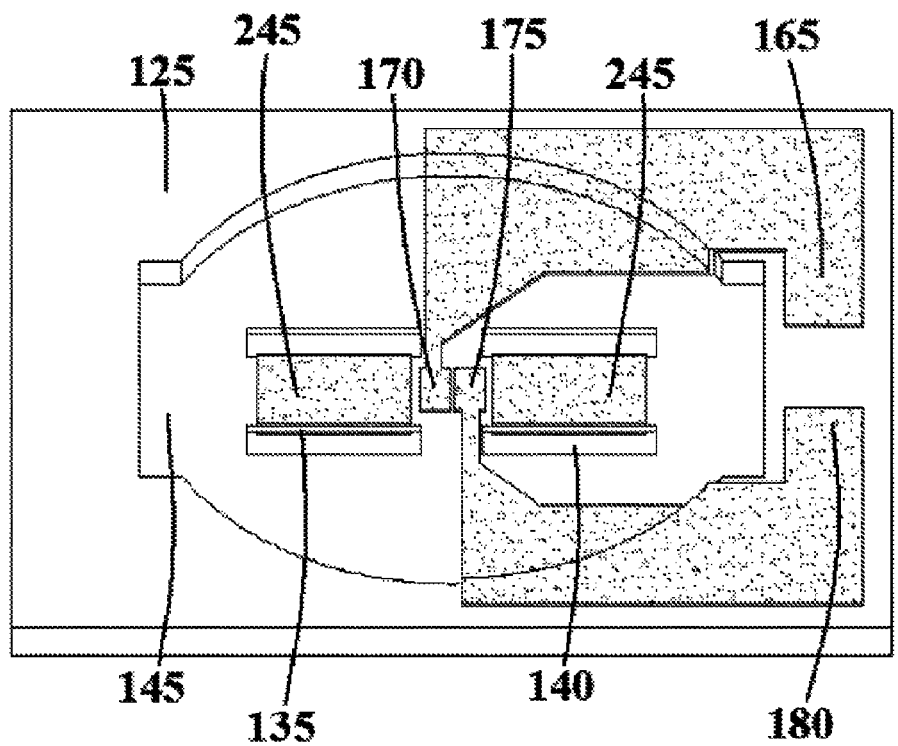
FIG. 10B is a bottom perspective view of the isolation bridge bulk acoustic wave (BAW) monolithic crystal filter (MCF) structure of FIG. 10A according to one embodiment of the present invention.
Figure 10C:
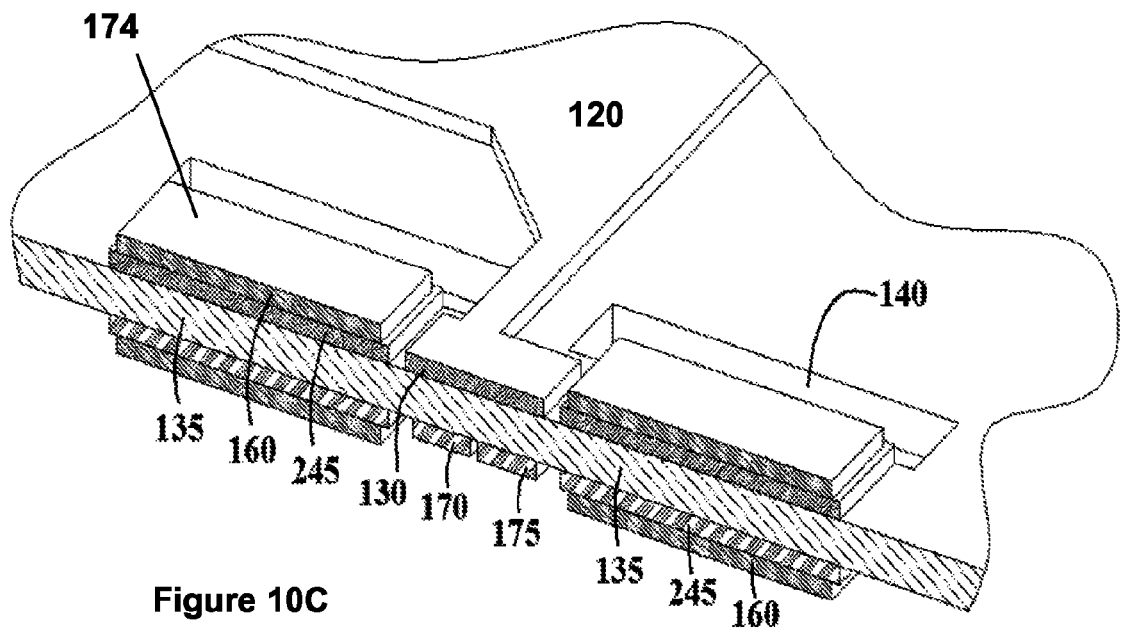
FIG. 10C shows a cut-away side perspective view of an isolation bridge bulk acoustic wave (BAW) monolithic crystal filter (MCF) structure according to one embodiment of the invention.

FIGS. 10A, 10B, and 10C, depict an isolation bridge BAW monolithic crystal filter (MCF) device. Such a structure is similar to the embodiment of FIG. 5A-5C, with the addition of the isolated segments about the bridge and separate from the active acoustic region formed with the electrodes 130, 170, 175. On the piezoelectric substrate 125 there is a ground electrical connection 120 coupled to a ground electrode 130 on one side of the substrate 125. On the other side of the substrate 125 are at least two positive electrodes, namely an input positive electrode 170 and an output positive electrode 175.

In this embodiment, an input positive electrical connection 165 is disposed on the substrate 125 and electrically coupled to an input positive electrode 170. On the opposing side is the ground electrode 130 with the piezoelectric bridge 135 therebetween which forms a first acoustic wave transducer. There is also an output positive electrical connection 180 coupled to an output positive electrode 175 having the ground electrode 130 on the opposing side and with the piezoelectric bridge 135 therebetween. This forms a second acoustic wave transducer.

There are sensing areas formed on either side of the central acoustic wave device as well as on both sides of the bridge 174 in this embodiment. These sensing areas are formed with the piezoelectric bridge 135 as the base, with an optional metallization layer 245 followed by an optional sensing film 160 (not shown for clarity).

As noted, the sensing films 160 can be disposed on the top and bottom surfaces of the isolated BAW structure for operation as a shear mode device. In addition, it should be understood that the orientation of the bridge with respect to the propagation direction can be at any angle depending upon the design criteria. Typically it is oriented for maximum response but there may be certain applications that have characteristics favorable for other orientations. The operation of the MCF was previously discussed for a full bridge and operation of the device is analogous on the isolation bridge.

One skilled in the art will realize that the electrodes of an MCF can be disposed in numerous other sequences and that the ground electrodes can be split into separate input and output ground electrodes.

Figure 11A:
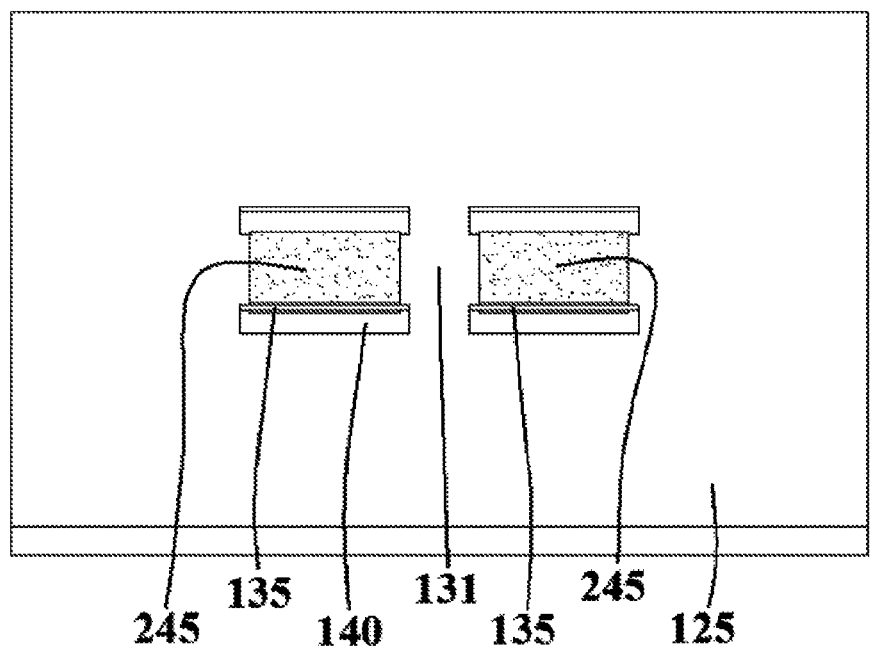
FIG. 11A is a top perspective view of an isolation bridge bulk acoustic wave (BAW) lateral field excitation (LFE) structure with a sensing film according to one embodiment of the present invention.
Figure 11B:
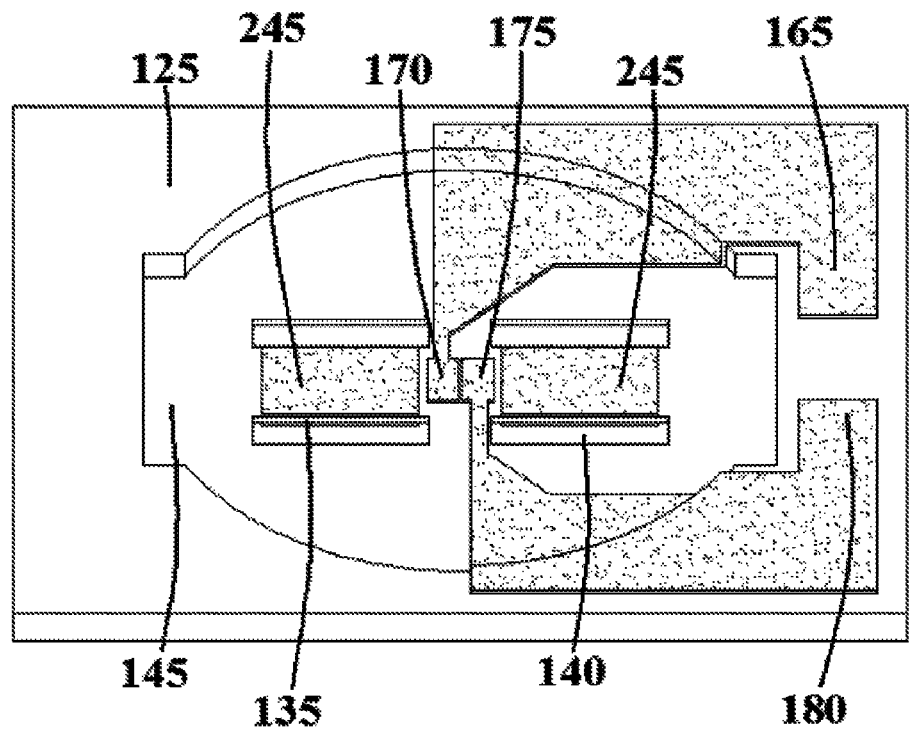
FIG. 11B is a bottom perspective view of the isolation bridge bulk acoustic wave (BAW) lateral field excitation (LFE) structure of FIG. 11a according to one embodiment of the present invention.
Figure 11C:
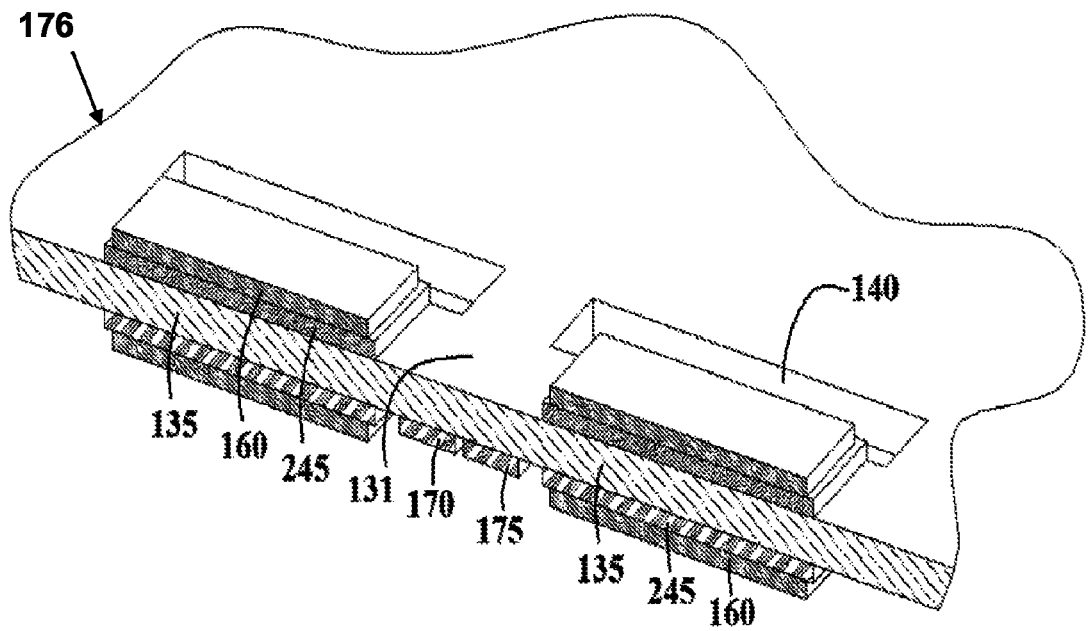
FIG. 11C shows a cut-away side perspective view of an isolation bridge bulk acoustic wave (BAW) lateral field excitation (LFE) structure according to one embodiment of the invention.

Referring to FIGS. 11A, 11B, and 11C, an isolation bridge bulk acoustic wave (BAW) lateral field excitation (LFE) structure is depicted. This embodiment is distinguished from the full bridge BAW LFE of FIG. 6A-6C by the multiple sensing films and structures disposed about the acoustic wave device formed by the electrodes 170, 175 and the opposing bare surface 131. The input positive electrode 170 and an output positive electrode 175 establishes the acoustic wave device subject to lateral field excitation (LFE) in which the acoustic waves traverse the device laterally between the two electrodes 170, 175. There are multiple sensing areas formed proximate the active acoustic wave region. The sensing areas are formed from the combination of the piezoelectric bridge 135, metallization layer 245 and sensing films 160. A plurality of sensing films 160 can be disposed on the piezoelectric bridge 176, wherein the sensing films 160 can be the same type in order to ensure greater response, or there can be different sensing films that respond to different target substances.

Figure 12A:
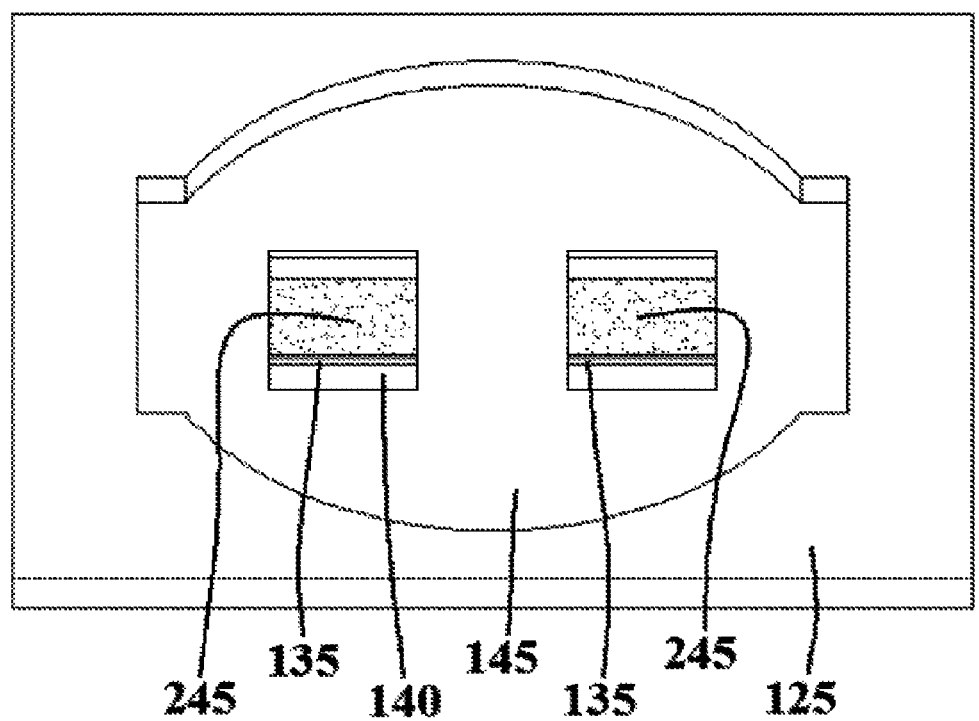
FIG. 12A is a top perspective view of an isolation bridge surface generated acoustic wave (SGAW) structure with a sensing film according to one embodiment of the present invention.
Figure 12B:
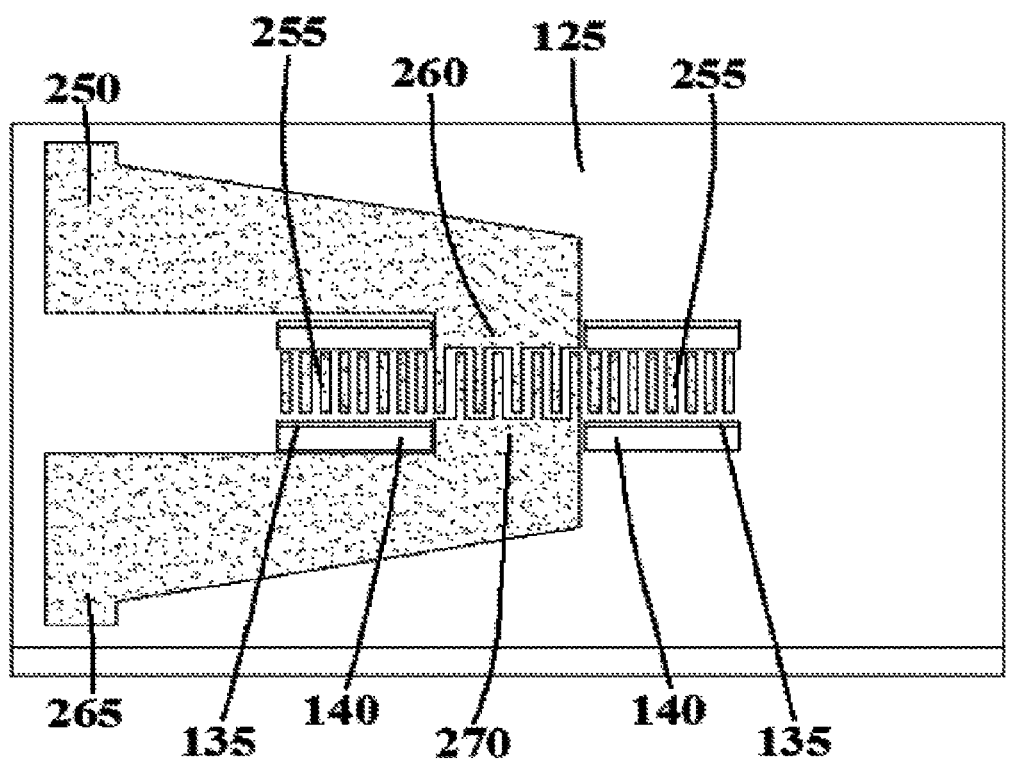
FIG. 12B is a bottom perspective view of the isolation surface generated acoustic wave (SGAW) structure of FIG. 12A according to one embodiment of the present invention.
Figure 12C:
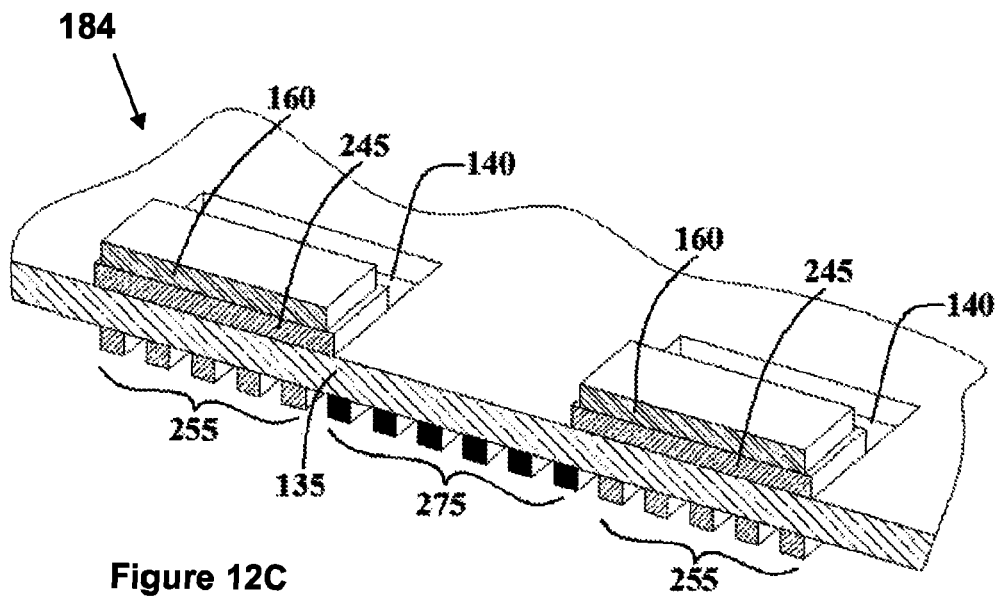
FIG. 12C shows a cut-away side perspective view of an isolation bridge surface generated acoustic wave (SGAW) structure according to one embodiment of the invention.

Referring to FIGS. 12A, 12B, and 12C, an isolated bridge surface generated acoustic wave (SGAW) structure is depicted. This embodiment is a one port device having reflectors; however a two port embodiment is within the scope of the invention, either as a delay line or a two-port resonator also having reflectors. The bridge 184 has a metalized surface 245 which is typically floating although it can be a ground plane. The acoustic wave bridge 184 is formed with etched relief section 140 on opposing sides of the bridge 176 wherein the bridge 184 is coupled firmly to the substrate 125.

There is a positive one-port electrical connection 250 coupled to the positive one-port bus bar 260. On the adjacent side there is negative one-port electrical connection 265 that is coupled to a negative one-port bus bar 270. A one-port inter digital transducer (IDT) 275 is electrically coupled to the positive one-port bus bar 260 and the negative one-port bus bar 270. One or more surface gratings 255 are disposed on the bridge 176 wherein the input interdigital transducer (IDT) 275 receives energy from some acoustic energy source. The surface gratings 255 do not need to have the same number of fingers or the same grating period as the IDTs 275.

Opposing the surface gratings 255 are the sensing areas, which in this embodiment have a metallization layer 245 disposed upon the piezoelectric bridge 135 and a sensing film 160 disposed upon the metallization layer 245. There may be multiple sensing films 160.

An alternate embodiment employs a two port IDT that provides for a separate input IDT and output IDT, which may include a center surface grating. Other embodiments include dispersive, non-dispersive, resonant, and delay line structures. Various other combinations and embodiments detailed herein can be implemented.

Figure 13A:
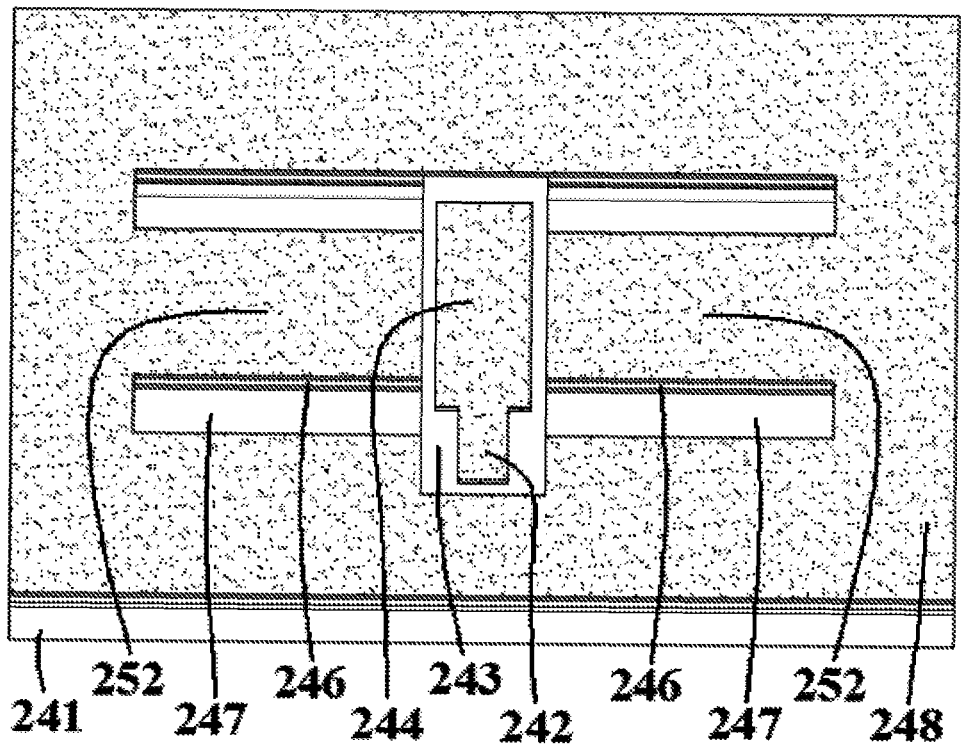
FIG. 13A is a top perspective view of an isolation bridge bulk acoustic wave (BAW) film bulk acoustic resonator (FBAR) structure with a sensing film according to one embodiment of the present invention.
Figure 13B:
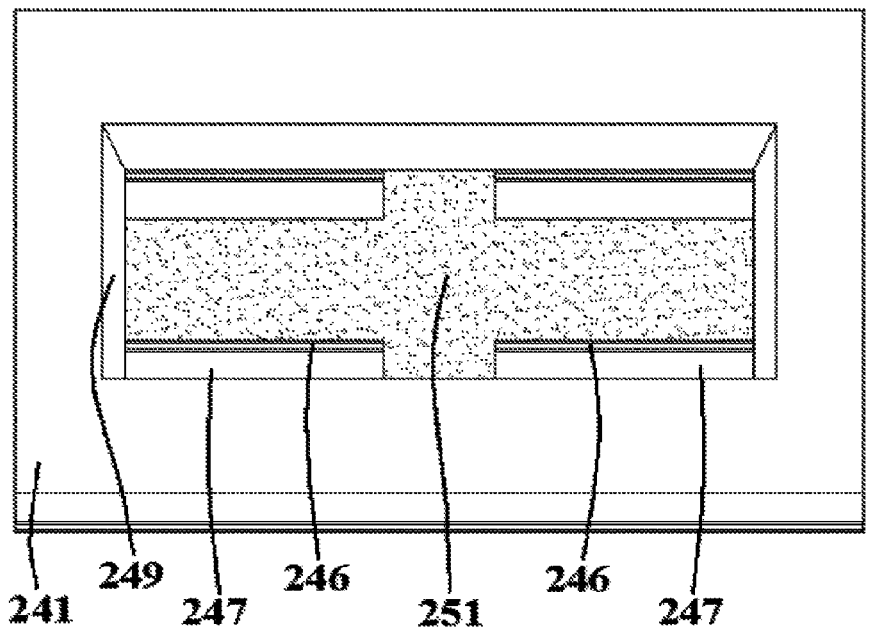
FIG. 13B is a bottom perspective view of the isolation bridge bulk acoustic wave (BAW) film bulk acoustic resonator (FBAR) structure of FIG. 13A according to one embodiment of the present invention.
Figure 13C:
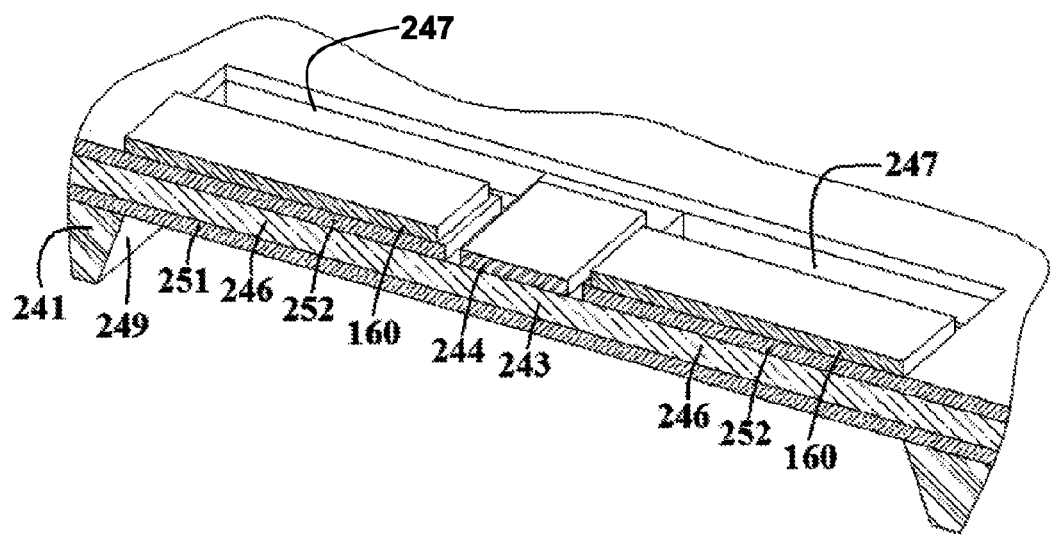
FIG. 13C shows a cut-away side perspective view of an isolation bridge bulk acoustic wave (BAW) film bulk acoustic resonator (FBAR) structure according to one embodiment of the invention.

Referring to FIGS. 13A, 13B, and 13C, an isolation BAW film bulk acoustic resonator (FBAR) is shown. The ground electrode 251 on one side of the bridge 172 is electrically coupled to a ground connection 248 typically by using vias (not shown) through the thin film piezoelectric layer 243. In this embodiment, a positive electrical connection 242 is disposed on the thin film piezoelectric layer 243 and electrically coupled to a positive electrode 244 with the FBAR piezoelectric bridge section 246 disposed beneath. The FBAR relief 247 defines the perimeter of the rectangular bridge structure 172 and the FBAR piezoelectric rectangular bridge 246 separates the positive electrode 244 and the ground electrode 251. A base substrate pocket 249 allows the bridge structure 172 to be suspended over an open area and coupled to the bridge ends for the firm support.

The bridge structure 172 of FIG. 8C illustrates one embodiment for the structure. The structure itself has a base substrate 241 with a base substrate pocket 249 defining the open area under the bridge 172. The ground electrode is 251 disposed on at least a portion of the base substrate and a portion of the ground electrode 251 is exposed to the open area of the pocket 249. On top of the ground electrode 251 is a thin film piezoelectric 243 covers at least a portion of the ground electrode 251. Substantially all of the thin film piezoelectric 243 is covered by a ground electrical connection 248 with the exception of the bridge section wherein there is a region without the ground electrical connection layer 247.

In the bridge section, the thin film piezoelectric is termed the bridge piezoelectric 246. The lower level of the bridge 172 is formed by the ground electrode 251 suspended over the base substrate pocket 249. The thin film piezoelectric bridge 246 is disposed over the ground electrode 251. A portion of the positive electrical connection 242 is disposed on the piezoelectric bridge 246 and the sensing film 160 is disposed upon the positive electrical connection 242. In the bridge region which is devoid of the ground electrical connection 248, there are FBAR relief structures 247 on the sides of the bridge 172.

Figure 14A:
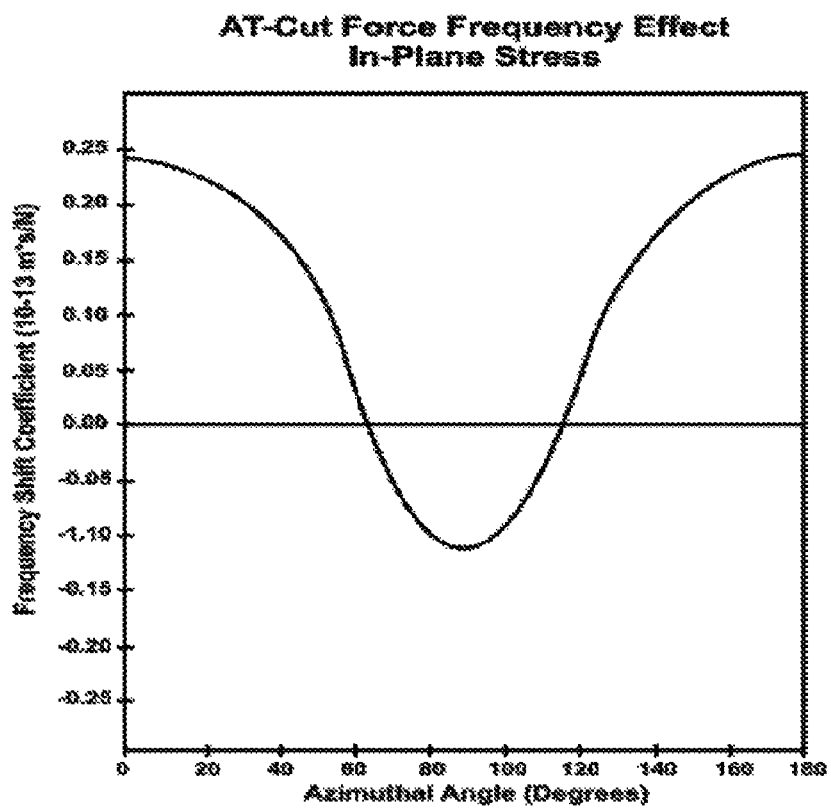
FIG. 14A shows a graphical depiction of the frequency shift versus the azimuthal angle illustrating the force frequency effect of in-plane stress.

Referring to the FIG. 14A, it has been demonstrated that there are optimal frequency change response as shown in the frequency response curve. Some of the embodiments herein include orienting the bridge for maximum sensitivity. Referring to "*Resonators for severe environments*" by T. J. Lukaszek and A. Ballato, Proc. 3$^{rd}$ Annual Symposium on Frequency Control, pp 311-321, 1979 which is incorporated by reference herein. There are optimal directions for sensitivity to stress and, for AT-cut quartz an alignment of the bridge along crystallographic X will be optimal for stress effects. Thus, the bridge device can be oriented along a certain azimuthal direction for stress effects optimized for any given substrate.

Figure 14B:
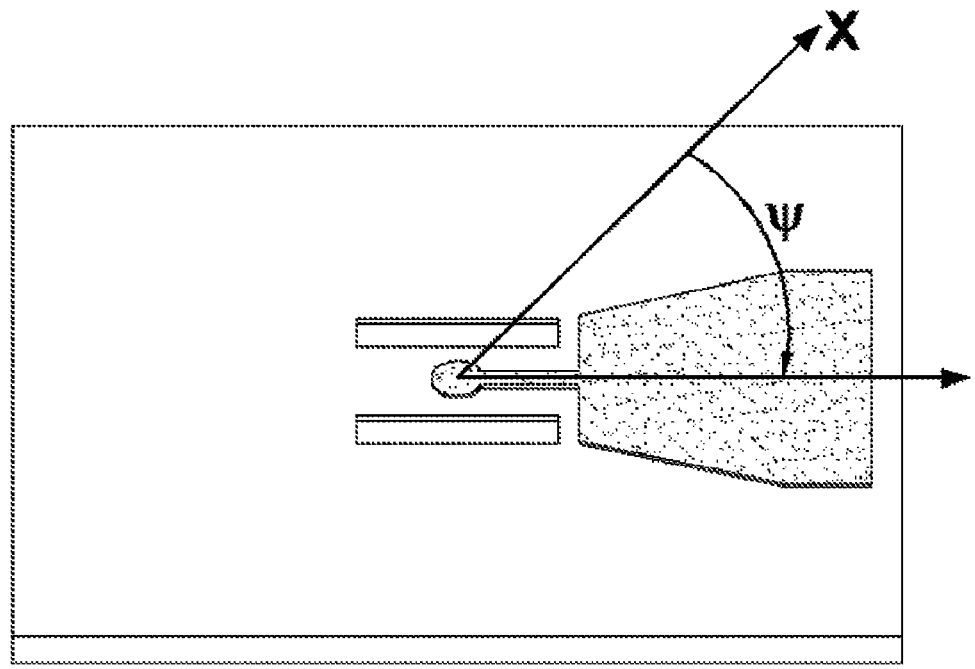
FIG. 14B shows a top perspective view of a full bridge bulk acoustic wave (BAW) structure with an angular alignment according to one embodiment of the invention.
Figure 14C:
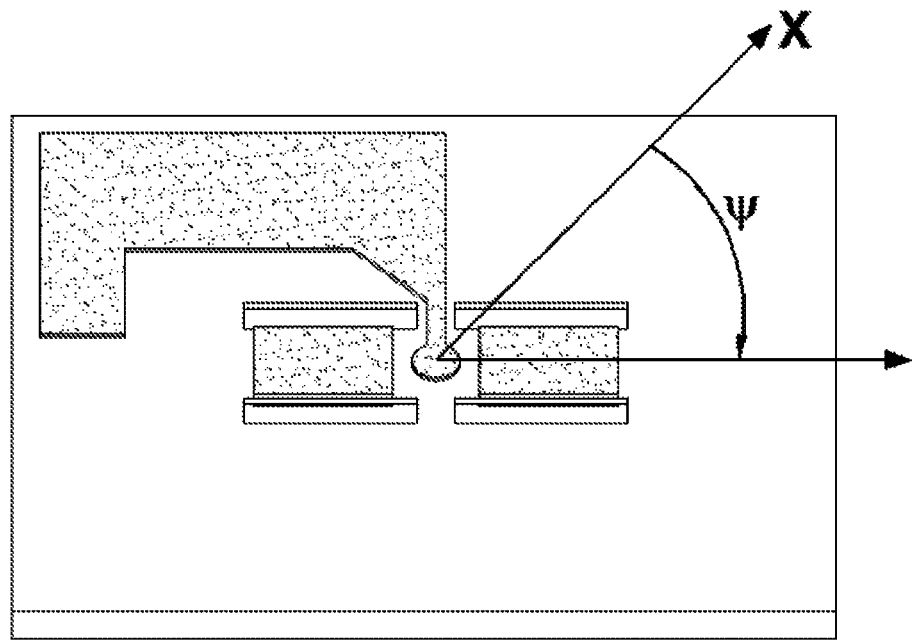
FIG. 14C shows a top perspective view of an isolation bridge bulk acoustic wave (BAW) structure with an angular alignment according to one embodiment of the invention.
Figure 14D:
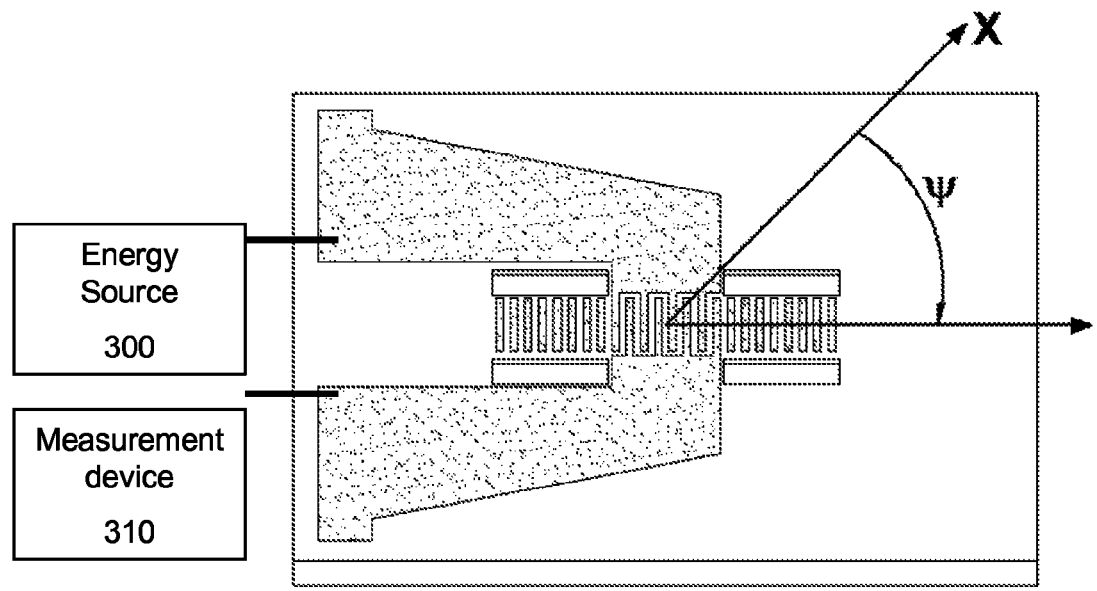
FIG. 14D shows a top perspective view of an isolation bridge surface generated acoustic wave (SGAW) structure with an angular alignment according to one embodiment of the invention.
Figure 14E:
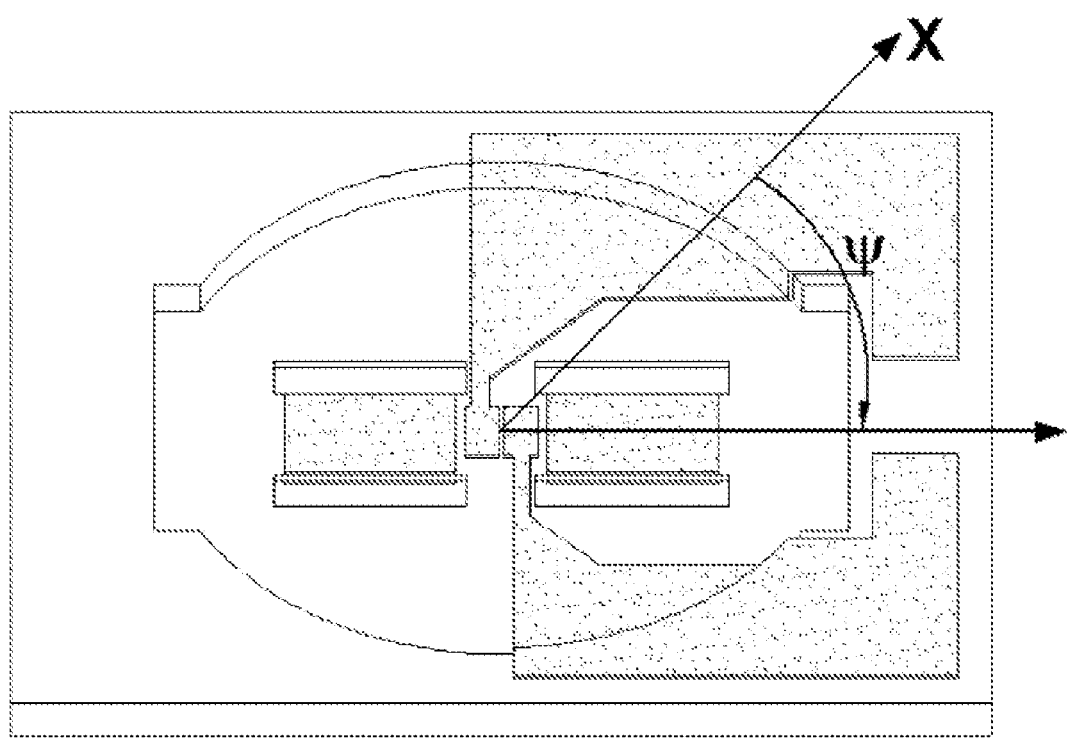
FIG. 14E shows a top perspective view of an isolation bridge bulk acoustic wave (BAW) monolithic crystal filter (MCF) structure with an angular alignment according to one embodiment of the invention.

Referring to FIGS. 14B, 14C, and 14D, these illustrate that there are angles ψ for stress wherein these angle alignment will provide tailored responses. According to one embodiment, the structure is designed so as to be optimized for the response curve according to the angular alignment for the full bridge and isolation bridge structures.

For each of the designs illustrated herein, there are other variations based bridge length or diameter and bridge alignment angle with respect to the crystalline x-axis. When the bridge is stressed, it will cause a corresponding change in the resonant frequency or propagation or coupling characteristics of the acoustic wave device. The resonant frequency or propagation or coupling characteristics of the bridge will typically be dependent on the stress and not the length of the bridge or the diameter of the bridge. This provides an advantage over other micromachined resonant structures because the present invention is able to make bridge structures that are much shorter in length or smaller in diameter while being substantially insensitive to small variations in manufactured dimensions. This fact, in turn, allows for the creation of arrays of bridges in a much smaller area than other competing bridge technologies with much higher process yield.

A stationary device can also incorporate the present sensing wherein the unit continuously monitors the environment and upon the triggering of a certain target matter, a notification is provided. As detailed herein, an array of bridge sensing devices can be deployed with respective acoustic wave devices for the detection of the gas(es) for a particular film. Multiple arrays with differing designs and differing films can be encompassed within a single housing such that multiple gases can be detected.

Referring again to FIG. 14D, the coupling of the acoustic energy source 300 and the measurement device 310 are depicted according to one embodiment. Electrical connectivity and the circuit configurations for generating the acoustic wave signals and measuring responses are well known in the art, including both wired and wireless implementations. Typically there is some energy source 300 which is then electrically coupled to the structure via electrical traces, vias, and busbars and therein converted to acoustic waves that are sensitive to the stress induced variations. According to a basic example intended to show a simple embodiment, there is an energy source 300 such as an oscillator circuit that provides the drive signal. The drive signal, which may be a stable frequency, is coupled to the structure via the electrical connections, which in turn is electrically coupled to the corresponding electrodes of the bridge device thereby providing the acoustic waves. The output response is electrically coupled in a similar manner via the electrodes and electrical connections to a measuring device 310, which can be a frequency measuring device. The difference in frequency based on movement of the bridge can be processed to determine the effects related to the sensing film.

As detailed herein, there are many embodiments and applications that can be implemented using the present invention. Some of these include the following: BAW Bridge—BAW Bridge Gas Sensors; and BAW Bridge Magnetic Sensors; and BAW Bridge Torque Sensors: SGAW Bridge—SGAW Bridge Gas Sensors; and SGAW Bridge Magnetic Sensors; and SGAW Bridge Torque Sensors: MCF Bridge—MCF Bridge Gas Sensors; MCF Bridge Magnetic Sensors; and MCF Bridge Torque Sensors: LFE Bridge—LFE Bridge Gas Sensors; and LFE Bridge Magnetic Sensors; and LFE Bridge Torque Sensors: FBAR Bridge—FBAR Bridge Gas Sensors; and FBAR Bridge Magnetic Sensors; and FBAR Bridge Torque Sensors. There may also exist pressure sensors in which a pressure applied to a membrane is transmitted as a normal force applied at a point or over a small region on the bridge. The distribution of stress from the point of contact creates a stress field defined by the shape of the bridge and the stresses alter the sensor frequency, providing an output that is proportional to the pressure applied to the membrane.

The full bridge structure presents a case in which the AWD is placed on the bridge whereas the isolation bridge structures describe a structure in which the AWD is placed between two bridges. Other locations for the AWD are readily seen to be responsive to the stresses induced by a perturbation to the bridge and any such placement can be described as being proximate to the bridge.

What is claimed is:

1. A system for acoustic sensing, comprising:
a bridge structure coupled to a substrate about at least two sides of said bridge structure, wherein said bridge structure includes a piezoelectric section and has at least one acoustic wave device (AWD) proximate a portion of said bridge structure, said AWD includes an active acoustic region; wherein a perturbation of said bridge structure produces stress effects measurable by said AWD;
wherein resonance of said AWD is independent of the intrinsic resonant flexural frequency of said bridge structure, and wherein said AWD is a bulk-generated acoustic wave (BGAW) device and operates by at least one of energy-trapping and thickness-resonance modes.

2. The system according to claim 1, further comprising a sensing material disposed on at least a portion of at least one surface of said bridge structure.

3. The system according to claim 2, wherein said sensing material is selected from at least one of the group consisting of: metal, metal oxide, metal nitride, ceramic, carbide, polymer, magnetic material, magnetostrictive material, electrostrictive material, and biological material.

4. The system according to claim 1, wherein said active acoustic region is a thickness field excitation (TFE) structure formed by at least one positive electrode disposed on one side of said bridge structure and at least one ground electrode on an opposing side of said bridge structure, and wherein an electrical energy source is coupled to said at least one positive electrode and said at least one ground electrode.

5. The system according to claim 4, wherein said thickness field excitation (TFE) structure is a two port device wherein a first transducer is electrically coupled to said electrical energy source by a first positive electrical connection and a first negative electrical connection and a second transducer provides a response related to an input electrical signal from said electrical energy source to a second positive electrical connection and a second negative electrical connection.

6. The system according to claim 1, wherein said active acoustic region is a lateral field excitation (LFE) structure formed by at least one positive electrode and at least one negative electrode electrically coupled on one side of said bridge structure and to an electrical energy source.

7. The system according to claim 1, wherein said bridge structure is a structure selected from at least one of the group consisting of: full bridge bulk acoustic wave, full bridge bulk acoustic wave monolithic crystal filter (MCF), full bridge bulk acoustic wave lateral field excitation (LFE), full bridge surface generated acoustic wave, full bridge film bulk acoustic resonator (FBAR), isolation bridge bulk acoustic wave, isolation bridge bulk acoustic wave MCF, isolation bridge bulk acoustic wave LFE, isolation bridge surface generated acoustic wave, and isolation bridge bulk acoustic wave FBAR.

8. The system according to claim 1, wherein said bridge structure is coupled to said substrate by one of the group consisting of: two supports and four supports.

9. The system according to claim 1, further comprising a measurement device coupled to said acoustic wave device (AWD) and measuring said stress effects.

10. A method for detecting a target substance, comprising:
forming a piezoelectric bridge having at least one acoustic wave device (AWD) disposed proximate a portion of said bridge, wherein resonance of said AWD is independent of the intrinsic resonant flexural frequency of said bridge, and said AWD is a bulk-generated acoustic wave (BGAW) device and operates by at least one of energy-trapping and thickness-resonance modes; exposing said bridge to some environment;
causing a stress response of said bridge from said environment; and
detecting a response of said acoustic wave device to said bridge stress response.

11. The method according to claim 10, further comprising disposing a sensing material on at least one portion of said bridge and allowing adsorption/absorption of said target substance by said sensing material.

12. The method according to claim 10, further comprising aligning said acoustic wave device at an angle ($\psi$) for a maximum change in frequency.

13. A sensing device for measuring stress effects, comprising:
a substrate having electrical connections disposed about said substrate and providing connectivity to an electrical energy source and a measurement device;
a bridge structure coupled to said substrate on a portion of at least two sides of said bridge structure comprising:
at least one acoustic wave device (AWD) formed proximate a portion of said bridge structure,
said acoustic wave device comprising a piezoelectric section with at least two electrodes disposed thereon, wherein resonance of said AWD is independent of the intrinsic resonant flexural frequency of said bridge structure, and said AWD is a bulk-generated acoustic wave (BGAW) device and operates by at least one of energy-trapping and thickness-resonance modes,
wherein a perturbation of said bridge structure causes a change in electrical properties of said acoustic wave device,
said change in electrical properties modifying a signal from said electrical energy source in a manner that is measurable by said measurement device.

14. The device according to claim 13, further comprising a sensing material disposed on at least a portion of at least one surface of said bridge structure causing said perturbation of said bridge structure.

15. The device according to claim 13, wherein said sensing device is selected from at least one of the group consisting of: bulk acoustic wave (BAW) bridge gas sensors, BAW bridge magnetic sensors, BAW bridge torque sensors, monolithic crystal filter (MCF) bridge gas sensors, MCF bridge magnetic sensors, MCF bridge torque sensors, film bulk acoustic resonator (FBAR) bridge gas sensors, FBAR magnetic sensors, and FBAR torque sensors.

16. The device of claim 13, wherein said piezoelectric section is selected from the group consisting of quartz, lithium niobate, lithium tantalate, langasite, aluminum phosphate, gallium phosphate, calcium-niobium-gallium-silicate, calcium-tantalum-gallium-silicate, strontium-niobium-gallium-silicate, strontium-tantalum-gallium-silicate, zinc oxide, aluminum nitride, and compositions thereof.

17. A system for acoustic sensing, comprising:
a bridge structure coupled to a substrate about a portion of at least two sides of said bridge structure, wherein said bridge structure includes a piezoelectric section and having at least one acoustic wave device (AWD) proximate a portion of said bridge structure,
wherein said AWD includes an active acoustic region,
wherein boundaries of said active acoustic region are decoupled from boundaries of said bridge structure;
an electrical signal coupled to said bridge structure,
wherein stresses induced in said bridge structure produce force-frequency effects measurable by said AWD;
wherein said force-frequency effects induce modulation of said electrical signal;
wherein resonance of said AWD is independent of the intrinsic resonant flexural frequency of said bridge structure, and said AWD is a bulk-generated acoustic wave (BGAW) device and operates by at least one of energy-trapping and thickness-resonance modes.

18. A sensing device for measuring physical parameters, comprising:
a substrate having electrical connections disposed about said substrate and providing connectivity to an electrical energy source and a measurement device;
a bridge coupled to said substrate on a portion of at least two sides of said bridge, said bridge comprising:
at least one acoustic wave device (AWD) formed proximate a portion of said bridge, said acoustic wave device comprising a piezoelectric section with at least two electrodes disposed thereon, wherein said bridge is responsive to stresses induced by application of a point force to said bridge,
wherein a bridge stress response causes a change in electrical properties of said acoustic wave device, said change in electrical properties modifying a signal from said electrical energy source in a manner that is measurable by said measurement device, wherein resonance of said AWD is independent of the intrinsic resonant flexural frequency of said bridge structure, and said AWD is a bulk-generated acoustic wave (BGAW) device and operates by at least one of energy-trapping and thickness-resonance modes.

19. The device according to claim 18, further comprising a diaphragm responsive to pressure disposed proximate said bridge, wherein said diaphragm transmits said point force.

20. The device according to claim 18, wherein magnetic fields acting upon a magnetic region proximate said bridge produce said point force.

21. The device according to claim 18, wherein an acceleration acting upon a proof mass proximate said bridge produces said point force.

* * * * *